(12) United States Patent
Khamene et al.

(10) Patent No.: US 7,949,385 B2
(45) Date of Patent: May 24, 2011

(54) SYSTEM AND METHOD FOR RECONSTRUCTION OF THE HUMAN EAR CANAL FROM OPTICAL COHERENCE TOMOGRAPHY SCANS

(75) Inventors: Ali Khamene, Princeton, NJ (US); Martin W. Masters, Belle Mead, NJ (US); Frank Sauer, Princeton, NJ (US); Therese Velde, Bridgewater, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1435 days.

(21) Appl. No.: 11/405,304

(22) Filed: Apr. 17, 2006

(65) Prior Publication Data
US 2006/0276709 A1    Dec. 7, 2006

Related U.S. Application Data

(63) Continuation-in-part of application No. 10/385,587, filed on Mar. 11, 2003.

(60) Provisional application No. 60/676,466, filed on Apr. 29, 2005.

(51) Int. Cl.
*A61B 5/05* (2006.01)

(52) U.S. Cl. ......... 600/416; 600/407; 600/160; 600/417
(58) Field of Classification Search .......... 600/101, 600/121, 200, 407, 160, 416, 417; 356/479
See application file for complete search history.

(56) References Cited

U.S. PATENT DOCUMENTS

| | | | |
|---|---|---|---|
| 2003/0103212 A1* | 6/2003 | Westphal et al. | 356/479 |
| 2004/0181128 A1 | 9/2004 | Masters | |

* cited by examiner

*Primary Examiner* — Brian Casler
*Assistant Examiner* — Joel M Lamprecht

(57) ABSTRACT

A method for reconstructing an ear canal from optical coherence tomography (OCT) scan data of an ear comprises extracting frame numbers and line numbers of interference intensities corresponding to one or more markers on an OCT scan guide, receiving reference frame numbers and lines numbers for one or more markers, determining a starting position and direction for the OCT ear scan from the ear scan marker frame and line numbers and the reference marker frame and line numbers, for each scan line, finding a pixel number of a maximum interference intensity value, and determining an offset distance of said pixel from said scan guide, and reconstructing a surface of the ear canal from the distance offset data.

29 Claims, 17 Drawing Sheets

| variable | name | typical value | correspondence |
|---|---|---|---|
| $d_0$ | scan line offset | 0 mm | |
| $d_s$ | sampling rate along scan line | 60 $\frac{pixel}{mm}$ | $d_n/z_{max}d = 1/\Delta z$ |
| v | probe speed | 0.5 $\frac{mm}{s}$ | |
| f | line sampling density | 1600 $s^{-1}$ | |
| $\omega$ | angular probe speed | 39.2 $\frac{rad}{s}$ | $fd_\alpha$ |
| $d_n$ | number of depth samples | 600-800 | |
| $f_d$ | frames per second | 6.25 $s^{-1}$ | |
| $N$ | lines per frame | 256 | $f/f_d$ |
| $d_\alpha$ | angular increment | 0.0245 rad | $2\pi/N$ |
| $\Delta x$ | transverse resolution | 0.2747 mm | $2\pi z_{max}/N$ |
| $z_{max}$ | scan radius | 11.2 mm | |
| $\Delta t$ | resolution along scan path | $3.125 \cdot 10^{-4}$ mm | $v/f$ |
| $\Delta z$ | axial resolution | 0.0179 mm | $z_{max}/d_n = 1/d_s$ |

FIG. 6

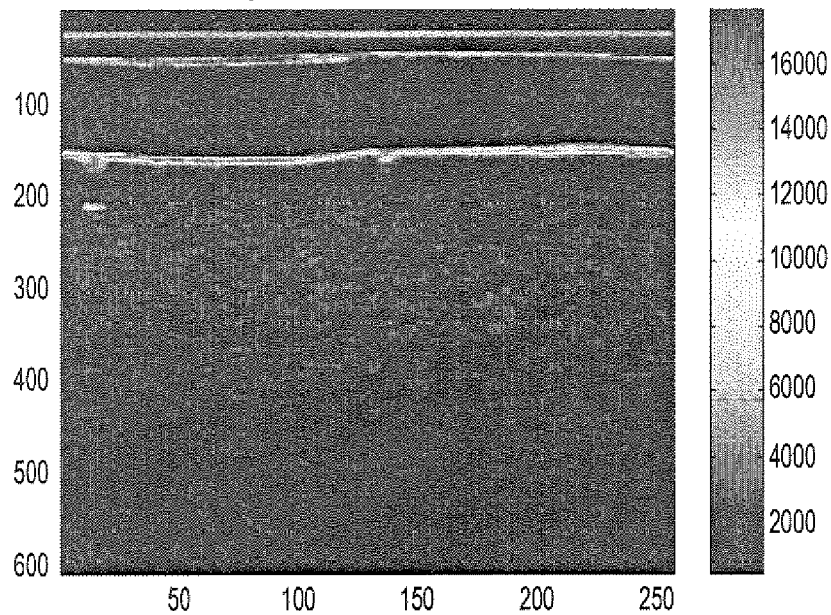
(a)
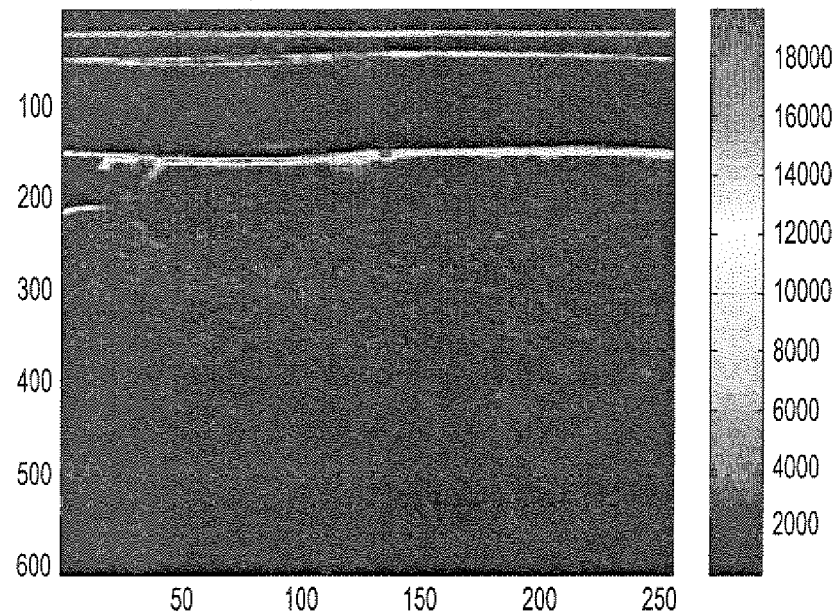
(b)
FIG. 12

| | Scan 489 | | Scan 490 | | Scan 491 | |
|---|---|---|---|---|---|---|
| Starting parameters | t [mm] | α[rad] | t [mm] | α[rad] | t [mm] | α[rad] |
| marker1 | 5.0584 | 1.4473 | 5.2534 | 4.1948 | 5.4150 | 4.3175 |
| marker2 | 4.9725 | 0.9812 | 5.3256 | 3.5816 | 5.4897 | 3.9005 |
| marker3 | 4.9700 | 0.7850 | 5.3253 | 3.5570 | 5.4875 | 3.7288 |
| average | 5.0003 | 1.0712 | 5.3015 | 3.778 | 5.464 | 3.9822 |

|  |  | marker1 | marker2 | marker3 |
|---|---|---|---|---|
| e0000487.oct | t in [mm] | 18.1313 | 31.8128 | 38.0556 |
| e0000493.oct | t in [mm] | 18.2109 | 31.9722 | 38.2159 |
|  | difference in [mm] | 0.0796 | 0.1594 | 0.1603 |
| e0000487.oct | $\alpha$ in [rad] | 4.0231 | 4.1458 | 4.3666 |
| e0000493.oct | $\alpha$ in [rad] | 3.9986 | 4.0967 | 4.3911 |
|  | difference in [rad] | 0.0245 | 0.0491 | 0.0245 |

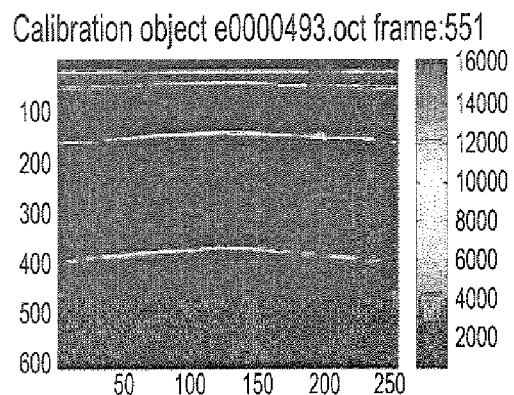
(a)
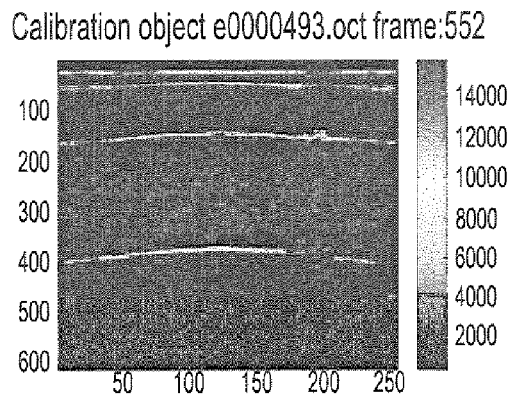
(b)
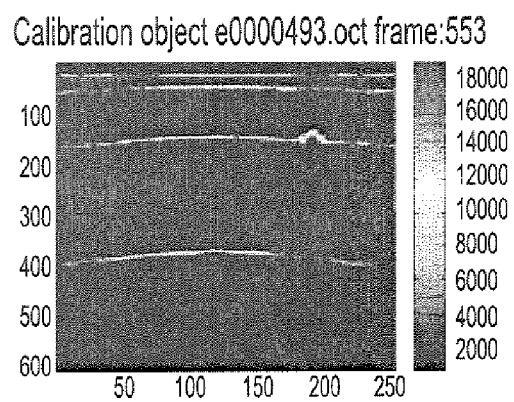
(c)
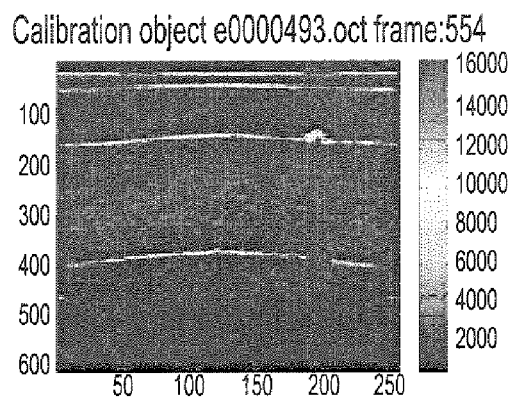
(d)
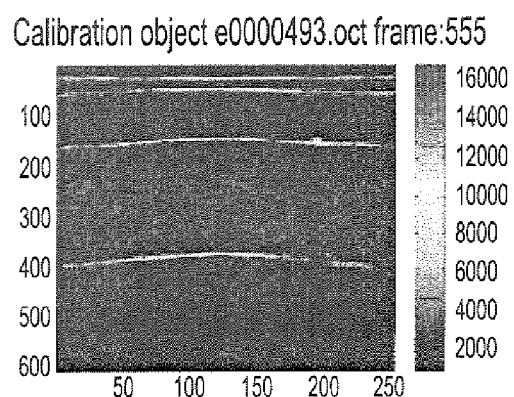
(e)
FIG. 16

SYSTEM AND METHOD FOR RECONSTRUCTION OF THE HUMAN EAR CANAL FROM OPTICAL COHERENCE TOMOGRAPHY SCANS

CROSS REFERENCE TO RELATED UNITED STATES APPLICATIONS

This application is a continuation-in-part of co-pending U.S. patent application Ser. No. 10/385,587, filed on Mar. 11, 2003, entitled originally entitled "Determining the geometry and dimensions of a three-dimensional object", and claims priority from "Reconstruction of the Human Ear Canal from Optical Coherence Tomography (OCT) Scans", U.S. Provisional Application No. 60/676,466 of Masters, et al., filed Apr. 29, 2005, the contents of the latter of which are incorporated herein by reference.

TECHNICAL FIELD

This invention is directed to imaging techniques for generating 3D models of the human ear.

DISCUSSION OF THE RELATED ART

Currently about 21 million people in the United States and 30 of every 1,000 school age children suffer from a hearing impairment. By age 65, one out of three people has a hearing loss and 75% of those who could benefit from hearing aids do not use them. People with hearing loss wait for an average of seven years before seeking help. Isolation, withdrawal, and depression are common reactions to hearing impairment. Moreover, hearing-impaired people have a much higher divorce rate than people whose hearing is not impaired. This situation indicates the need to approximate the natural hearing process as closely as possible with technical means. The human hearing organ has evolved to be able to take in acoustical communication in the environment, even under extreme conditions. Years of research have uncovered many of nature's secrets concerning the hearing process. This knowledge provides a basis for the technical development of modern hearing aids. Technology involved in hearing instruments, as in all medical fields, is continually improving.

Hearing instruments come in a variety of sizes. Each hearing aid user needs a custom-made hearing aid shell for proper fit and function and any hearing instrument requires a model of the ear to ensure a good fit. Currently, the physician takes a physical impression of the ear by placing a small foam block in the ear canal. The canal is then filled with a silicone material. After several minutes, the material is removed and the impression is then sent to an earmold lab or hearing aid manufacturer where it is scanned to create a 3D data file. This 3D representation of the ear canal and concha can be used to form the outer shell of the custom-fitted hearing aid manufactured for the patient. However, the current method is very technique sensitive and therefore inaccuracies of the molded impressions are not rare. Thus, it is desired to develop a proprietary scanning device to capture an accurate "point cloud" of digital data representing the ear cavity geometry of a patient being fitted with an In-The-Ear (I-T-E) hearing aid. Furthermore, as the impressions have to be transported to the hearing aid manufacturer, transportation costs and time delays are inevitable. There are also errors and labor costs that arise from the labor-intensive process of converting the information contained in the impression into a finished hearing instrument. By placing an I-T-E Scanning Device in the physician's office, a "point cloud" set of geometric data for each ear canal and concha could be rapidly collected and, for example, be emailed to the hearing aid manufacturer via Internet.

Optical Coherence Tomography (OCT) is an emerging high-resolution imaging technology that can perform high resolution, real-time cross-sectional imaging of tissue. OCT can be used as a type of "optical biopsy" to perform minimally-invasive imaging up to a depth of 2-3 mm with resolutions as high as 10 µm in commercially available systems. OCT uses near-infrared light which can be used in fiber optic devices such as catheter probes and imaging needles. This novel imaging technology has the potential to improve cancer detection and diagnosis and is particularly useful in opthalmology due to the optical properties of the eye and the accessibility of the retina for examination through the pupil. OCT also has the potential to provide measurements for a 3D model of the human ear. An OCT scanner can be used for collecting series of cross-sectional images. These 2D images can then be compounded into a 3D volume and the ear's surface can be extracted. The 3D point cloud file representing the human ear canal and concha can then be used for creating custom-built hearing instruments.

OCT is analogous to ultrasound imaging, measuring the intensity of infrared light instead of acoustical waves. Whereas ultrasound pulse propagation and detection can be described in terms of time delay, OCT uses an interferometric correlation technique known as low-coherence interferometry to perform high-resolution measurements of the echo time delay of backscattered light. As the velocity of light is extremely high, it is not possible to measure directly the echo time delay of reflections electronically.

As mentioned above, OCT combines the principles of ultrasound with the imaging performance of a microscope and a form factor that is familiar to clinicians. Whereas ultrasound produces images from backscattered sound "echoes", OCT uses infrared light waves that are reflected from the microstructure within living tissues. Cross-sectional images generated by OCT are similar to those of ultra-sound imaging, but the image resolution of OCT is 1 to 15 µm, up to 2 orders of magnitude higher than conventional ultrasound. Although the imaging depth of OCT is limited by the light scattering and attenuation properties of tissue, image penetration of 2 or 3 mm can be achieved in most non-transparent samples. In transparent tissues including the eye, probing depths exceeding 2 cm have been demonstrated. It is indisputable that ultrasound techniques can provide information from depths far beyond the capability of OCT, but in many applications the resolution is not sufficiently satisfactory to result in any useful information. Moreover, there must be physical contact between the ultrasound instruments and the tissue being examined whereas OCT does not require a transducting medium and thus imaging can be performed directly through air.

Another advantage of OCT is that it enables one to look at structures without the need to perform a biopsy. For excisional biopsy and histopathology the clinician removes a specimen of tissue which is then sectioned into thin slices and examined under a microscope. In contrast to conventional biopsy methods, OCT can image tissue in situ and in real time with a resolution approaching that of histopathology. In many situations, for instance in the brain, the standard excisional biopsy method can be extremely dangerous, hazardous or even impossible and can then be replaced by OCT scanning. As OCT technology can be readily interfaced with optical fiber techniques to catheters, endoscopes, laparo-scopes and surgical probes, it can be carried out at virtually any site in the body using non-invasive and minimally-invasive procedures.

SUMMARY OF THE INVENTION

Exemplary embodiments of the invention as described herein generally include methods and systems for generating 3D models of the human ear using Optical Coherence Tomography (OCT). OCT performs high-resolution, cross-sectional tomographic imaging of the internal microstructure in materials and biological systems by measuring backscattered or backreflected light. An OCT scanner is used to collect series of cross-sectional images, to compound these 2D images into a 3D volume and to extract the ear's surface, to provide an accurate model of the ear canal and concha for appropriate shaping of hearing aids. The reconstruction process requires the knowledge of two important scanning parameters: the position of the probe head and the direction in which the light is emitted and reflected throughout the scanning process. A calibration method for a reliable determination of these scanning parameters was devised. The evaluation of the developed process shows that the correct parameters are calculated and the canal of the ear can be reconstructed with satisfying results. The 3D point cloud file representing the human ear canal and concha can then be used for creating custom-built hearing instruments.

According to an aspect of the invention, there is provided a method for reconstructing an ear canal including providing a set of optical coherence tomography (OCT) scan data of an ear comprising frames and scan lines of pixels that form a 3D data set whose values are interference intensities, extracting frame numbers and line numbers of interference intensities corresponding to one or more markers on an OCT scan guide, receiving reference frame numbers and lines numbers for said one or more markers, determining a starting position and direction for said OCT ear scan from the ear scan marker frame and line numbers and said reference marker frame and line numbers, for each scan line, finding a pixel number of a maximum interference intensity value, and determining an offset distance of said pixel from said scan guide, and reconstructing a surface of said ear canal from said distance offset data.

According to a further aspect of the invention, an offset distance d of a pixel j from the guide is computed from $$d(j) = d_0 + \frac{j}{d_s},$$

wherein $d_0$ is an offset from the center of the guide and $d_s$ is a sampling rate.

According to a further aspect of the invention, the ear canal surface can be reconstructed from $$\vec{p}(i,j) = \vec{p}_0 + \vec{c}(t) + d(j)(\sin(\alpha)\vec{u} + \cos(\alpha)\vec{v}),$$

wherein $\vec{p}(i,j)$ represents a scan line i perpendicular to guide, j a pixel along the scan line, $\vec{p}_0$ is a starting position in space of the scan, $\vec{c}(t)$ a curved path of the guide, t is a position on the guide corresponding to the scan line i, and $\alpha$ is a scan line angle, and $\vec{u}$ and $\vec{v}$ are two unit vectors perpendicular to each other defining a 2D coordinate frame in a plane perpendicular to the curve $\vec{c}(t)$.

According to a further aspect of the invention, $$t = i \cdot \frac{v}{f},$$

wherein v is a scan speed of a scanning probe contained within said guide, and f is a scan line sampling frequency, and $$\alpha = i \cdot \frac{\omega}{f},$$

wherein $\omega$ is the angular speed of rotation the probe.

According to a further aspect of the invention, the unit vectors $\vec{u}$ and $\vec{v}$ are defined by $$\vec{u} = \frac{\vec{t} \times \vec{w}}{|\vec{t} \times \vec{w}|},$$

$$\vec{v} = \vec{t} \times \vec{u},$$

wherein $\vec{w}$ is a vector that is not perpendicular to the curve $\vec{c}(t)$ at any time, and $\vec{t}$ is a tangent to the curve defined as $$\vec{t} = \frac{d}{dt}\vec{c}(t).$$

According to a further aspect of the invention, the OCT scan data is obtained by providing an OCT scanning apparatus including a guide containing a rotatable probe, sliding and rotating said probe in said guide, emitting near infrared light from said probe at predetermined intervals, measuring interference of reflected light with a reference signal, and saving said interference data in a computer readable storage medium.

According to a further aspect of the invention, the method comprises, for each scan line, selecting those pixels with an interference intensity value above a pre-determined threshold and determining an offset distance of said selected pixels from said scan guide.

According to a further aspect of the invention, the method comprises, prior to finding a pixel number of a maximum interference intensity value for a scan line, discarding the intensity values at the beginning of a scan line, wherein said beginning values correspond to reflections from the scan guide itself.

According to a further aspect of the invention, the reference marker frame numbers and lines numbers were extracted from OCT scan data of a calibration object.

According to a further aspect of the invention, extracting said reference marker frame numbers and lines numbers from OCT scan data of a calibration object comprises providing a set of optical coherence tomography (OCT) scan data of a calibration object marked to indicate an angular direction of 0, said scan data comprising frames and scan lines of pixels that form a 3D data set whose values are interference intensities acquired using a calibration guide comprising one or more markers on said guide, extracting frame numbers and line numbers of interference intensities corresponding to said markers on said calibration guide, and determining spatial positions of said markers on said calibration guide from said frame number and said line numbers.

According to a further aspect of the invention, the marker positions on the guide are calculated from:

$$\alpha_{marker} = \begin{cases} 2\pi - (n_{S_{\alpha=0}} - n_{S_{marker}}) \cdot d_\alpha, & \text{if } n_{S_{\alpha=0}} > n_{S_{marker}} \\ (n_{S_{marker}} - n_{S_{\alpha=0}}) \cdot d_\alpha, & \text{if } n_{S_{\alpha=0}} \le n_{S_{marker}} \end{cases}$$

$$t_{marker} = ((n_{F_{marker}} - n_{F_{start}}) \cdot N + (n_{S_{marker}} - n_{S_{start}})) \cdot \Delta t,$$

wherein α is an angle of rotation about said guide, $\alpha_{marker}$ is an angular direction of a marker, $t_{marker}$ is the frame number of the marker, $n_{S_{\alpha=0}}$ is a line number of a scan line at an angular direction of 0, $n_{S_{start}}$ is a starting line number, $n_{S_{marker}}$ is a line number of a scan line that contains marker interference intensity values, $n_{F_{start}}$ is a starting frame number, $n_{F_{marker}}$ is a frame number of a frame containing marker interference intensity values, $d_\alpha$ is an angular increment, N is a number of lines per frame, and $\Delta t$ is a resolution along the scan path.

According to a further aspect of the invention, the starting position $t_{start}$ and direction $\alpha_{start}$ are computed from a marker position $t_{marker}$ and direction $\alpha_{marker}$ from $$\alpha_{start} = \begin{cases} \alpha_{marker} - n_{S_{marker}} \cdot d_\alpha, & \text{if } \alpha_{marker} - n_{S_{marker}} \cdot d_\alpha \geq 0, \\ 2\pi + \alpha_{marker} - n_{S_{marker}} \cdot d_\alpha, & \text{if } \alpha_{marker} - n_{S_{marker}} \cdot d_\alpha < 0, \end{cases}$$

$$t_{start} = t_{marker} - ((n_{F_{marker}} - 1) \cdot N + n_{S_{marker}}) \cdot \Delta t,$$

wherein $n_{S_{marker}}$ is a line number of a scan line that contains marker interference intensity values, $n_{F_{marker}}$ is a frame number of a frame containing marker interference intensity values, $d_\alpha$ is an angular increment, N is a number of lines per frame, and $\Delta t$ is a resolution along the scan path.

According to another aspect of the invention, there is provided a program storage device readable by a computer, tangibly embodying a program of instructions executable by the computer to perform the method steps for reconstructing an ear canal.

BRIEF DESCRIPTION OF THE DRAWINGS

FIG. 6 is a table of physical quantities that characterize OTC, along with exemplary values, according to an embodiment of the invention.

FIG. 12(a) depicts the last frame in which light reflections from section 1 of the calibration object can be observed, according to an embodiment of the invention.

FIG. 12(b) depicts the first frame in which light reflections from the cone-shaped surface can be perceived, according to an embodiment of the invention.

FIGS. 16(a)-(e) show the appearance of the laser marked crosses in the calibration scan, according to an embodiment of the invention.

DETAILED DESCRIPTION OF THE PREFERRED EMBODIMENTS

Exemplary embodiments of the invention as described herein generally include systems and methods for the extraction of the ear surface using OCT scanning data and 3D reconstruction algorithms and evaluation procedures.

OCT performs imaging by measuring the echo time delay and intensity of backscattered and backreflected light using an interferometric correlation technique. Light from a light emitting diode (LED) is coupled into an optical fiber. The light is coupled out in a sideway beam and the reflected and backscattered light is coupled back into the optical fiber. The optical fiber rotates to scan a plane and needs to be translated to measure a 3D volume. A sleeve guiding the rotating fiber is used to move the fiber along a certain scan path. If one can extract the distances from the fiber to the surface out of the scan data and if one knows the parametric curve function of the scan path, one can compute a 3D representation of the scanned ear surface.

Figure 1:
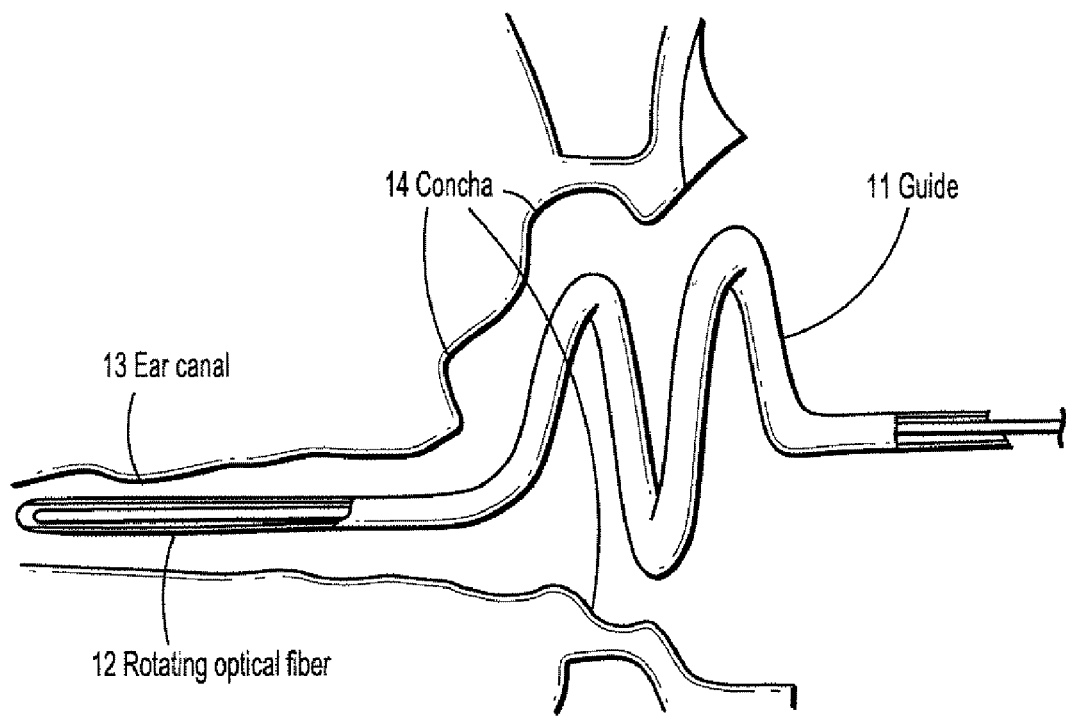
FIG. 1 depicts an exemplary OCT configuration for scanning an ear, according to an embodiment of the invention.

FIG. 1 depicts an exemplary OCT configuration for scanning an ear, according to an embodiment of the invention. Referring to the figure, a guide 11 containing a rotating optical fiber 12 is inserted into a concha 14 and ear canal 13. In order to build different kinds of hearing aids, the whole ear, including the canal and concha, should be scanned. It is desired that the measured shape be accurate to about 0.1 mm. Due to the limited range of the OCT system, the outer ear should be scanned using a curved sleeve guiding the fiber so that the scan path more closely resembles the ear shape.

One issue that arises when using a curved sleeve is that the position where the scan starts and the direction in which the light is first sent out should be known in order to perform 3D reconstruction. If a straight guide is used these two parameters are not important as it does not make a difference for the 3D reconstruction where the scan starts on the straight path. But when using a curved guide these parameters should be determined from a calibration procedure for extracting these parameters from the OCT scan data. A guide with special markings on it that appear in the OCT scan data can be calibrated, where the marking data provides information about the unknown parameters.

Physical Basics

Figure 2:
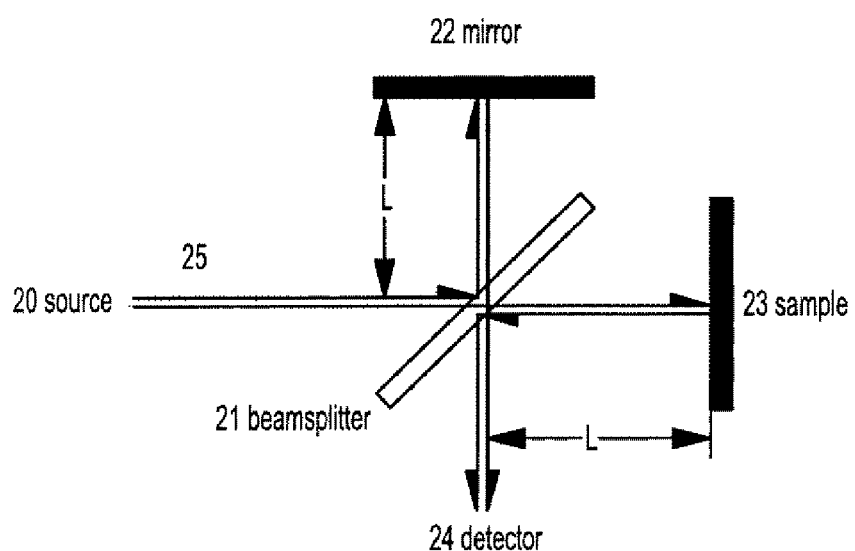
FIG. 2 depicts an exemplary OCT system using low-coherent light coupled into a fiber-optic interferometer, according to an embodiment of the invention.

An exemplary OCT system using low-coherent light from a broad bandwidth superluminescent diode (SLD) coupled into a fiber-optic Michelson interferometer is shown in FIG. 2. Referring to the figure, a light source 20 emits a near infrared beam 25 that is split by a fiber coupler 21 with half sent to a reference arm 22 and half sent to the sample arm 23. The reference beam is reflected from a mirror at a known distance and returns to the detector 24. The sample beam is retroreflected from different layers within the tissue being examined. By using a low-coherence light source and measuring the interference between light reflected from the tissue and the reference mirror, information on where the photons were backscattered from inside the sample can be extracted.

Since the coherence length of the light source is very short, interference only takes place if signal and reference path length are equal. If they are different, there is no interference. By moving the mirror in the reference arm and thus changing the distance that light covers in the reference arm, the intensity of the interference of light backscattered from different points within the tissue is recorded and a longitudinal scan of the sample is performed. The interferometric signal is demodulated using bandpass filtering and envelope detection, then digitized and stored on a computer for post-processing. OCT systems have a sensitivity up to −100 dB, meaning that reflected signals as small as $10^{-10}$ of the incident optical power can be detected. To receive data for a two-dimensional image, a series of longitudinal scans is performed with the optical beam position translated laterally between scans. The data set is then represented as either false-color or gray-scale image.

Figure 3:
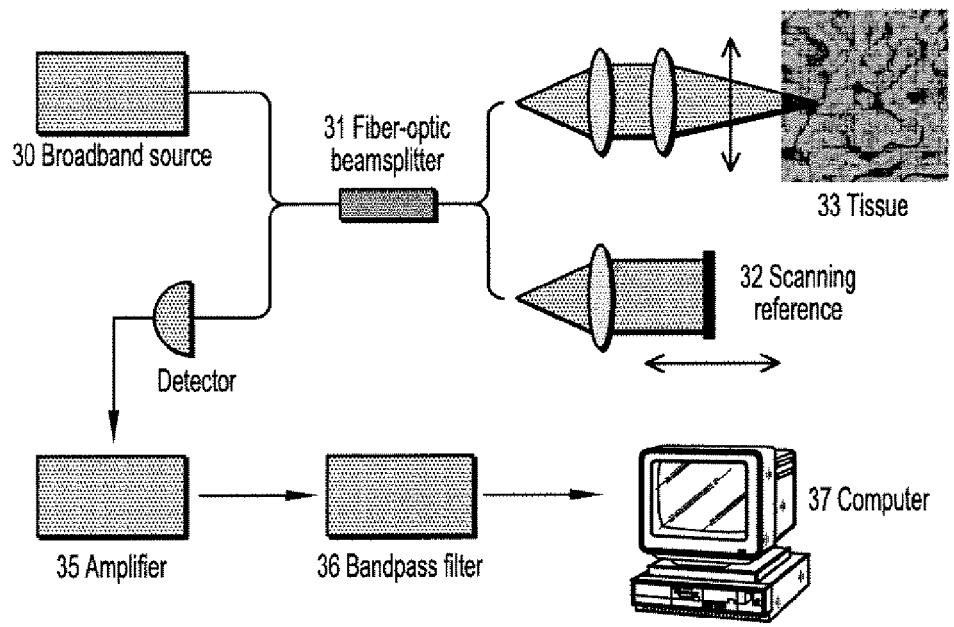
FIG. 3 is a schematic of a complete OCT system, according to an embodiment of the invention.

A schematic of a complete OCT system is shown in FIG. 3. Referring to the figure, a broadband infrared source 30 emits a near infrared beam that is split by a fiber optic beamsplitter 31 with half sent to a scanning reference mirror 32 and half sent to the tissue sample 33. The reference beam is reflected from the mirror 32 at a known distance and returns to the detector 34 where it interferes with light backscattered from different points within the tissue sample 33. The interferometric signal is amplified by amplifier 35, demodulated by bandpass filter 36, then digitized and stored on computer 37.

Figure 4:
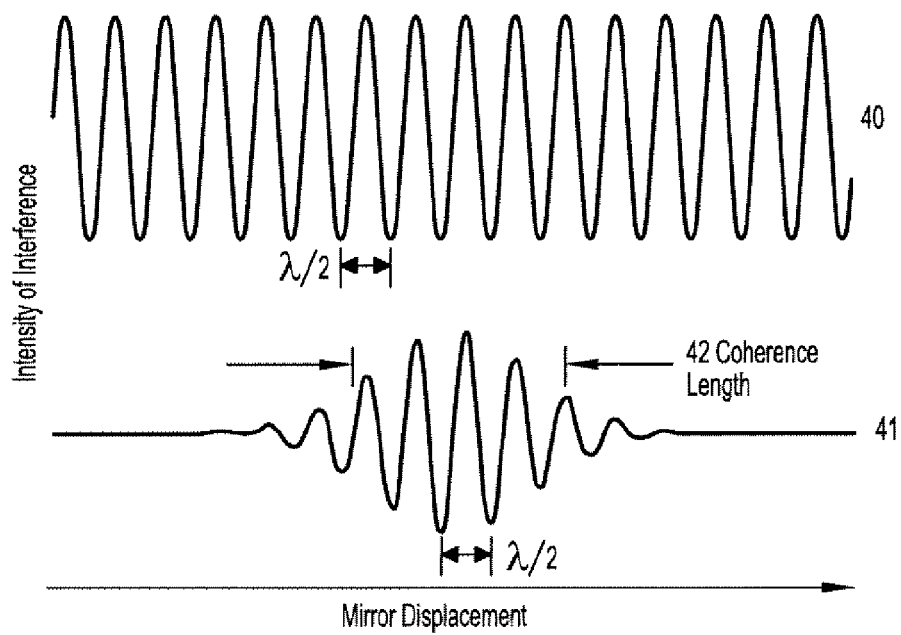
FIG. 4 compares the interferometric signals caused by coherent light with low-coherence light, according to an embodiment of the invention.

Due to the low-coherence light source, the signal falls off rapidly with delay mismatches, so that spatial characteristics can be extracted with very high precision. FIG. 4 compares the interferometric signals caused by coherent light on the one hand and low-coherence light on the other hand are compared in order to demonstrate how low-coherent light can be used to determine the positions of backreflection with high resolution. The top signal 40 depicts the interference that would be observed on the screen for a highly coherent source when the mirror in the Michelson interferometer setup is moved further and further back. The graph displays interference intensity of the signals as a function of mirror displacement. The bottom signal 41 depicts the interference that would be observed when using a low-coherence light source, indicating the coherence length 42. Since the interference associated with low-coherence interferometry can only be observed when the optical path lengths of the two arms of the interferometer are matched exactly, the setup can be applied as a method of distance measurement.

The depth resolution in OCT is defined by the coherence length of the light source. The coherence length $L_c$ for a light source having a Gaussian spectrum is given by $$L_c = \frac{\lambda^2}{n \cdot \Delta \lambda},$$

where $\lambda$ is the center wavelength, $\Delta\lambda$ is the full-width half-maximum (FWHM) spectral bandwidth and n is the index of refraction. The image depth resolution $\Delta z$ defined as $$\Delta z = \frac{2 \cdot \ln(2)}{\pi} \cdot \frac{\lambda^2}{n \cdot \Delta \lambda}$$

is proportional to the coherence length and thus inversely proportional to the bandwidth of the light source.

The depth resolution is mostly micrometer-scale depending on the center wavelength and the bandwidth of the used light source. Optical imaging of non-transparent tissues presents challenges due to scattering and absorption of tissue. The attractive spectral region for OCT imaging is the near infrared (NIR) at a wavelength of about 1.3 µm where light scattering is low with respect to visible light and tissue absorption is low as well, permitting a penetration up to a depth of 3 mm to be achieved.

Surface Extraction

According to one embodiment of the invention, exemplary experimental scans were acquired using a LightLab Optical Coherence Tomography Imaging—System Model M2-Cardiology. This OCT system operates at a wavelength of 1295 nm that is generated by a superluminescent LED producing light intensity of 11 mW measured at the patient interface unit.

Figure 5:
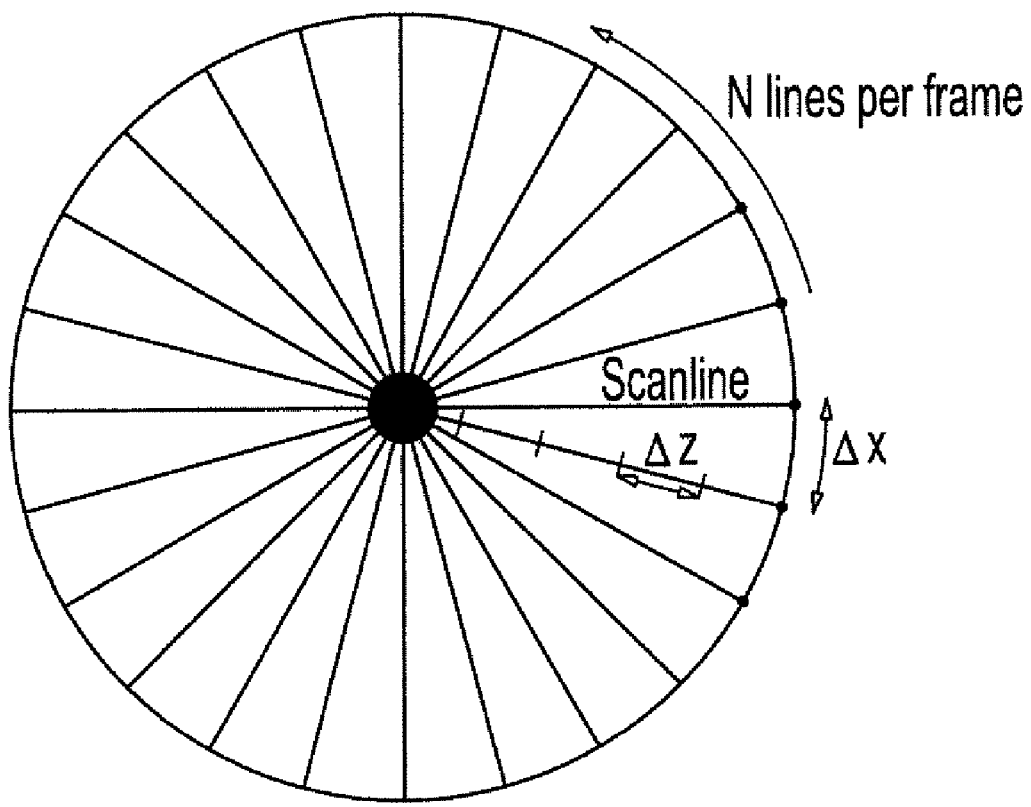
FIG. 5 is a schematic of an exemplary OTC imaging geometry, according to an embodiment of the invention.
Figure 7:
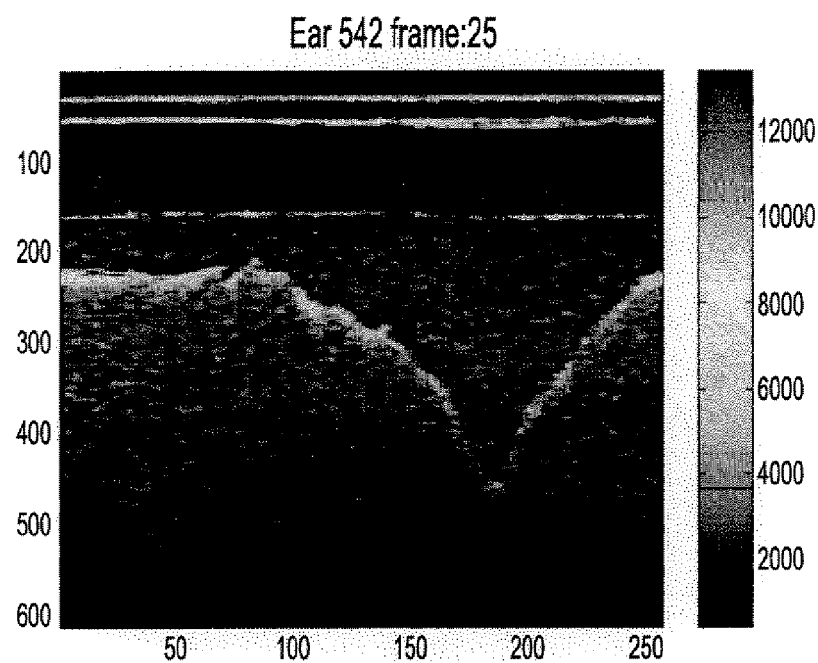
FIG. 7 depicts an exemplary TIFF image frames obtained from an OCT scan, according to an embodiment of the invention.

To scan the whole volume of the ear canal and the concha, the optical fiber in which the light from a SLD is coupled is simultaneously rotated and pulled back in a straight sleeve. An exemplary, non-limiting speed is about 0.5 mm per second. The measured scan lines are placed on a tight spiral with a resolution of 3.125%$10^{-4}$ mm along the scan path and an angle resolution of 1.4063 degrees. The depth of field (DOF) that can be scanned with such an OCT device is 11.2 mm which leads with 625 samples per line to a depth resolution of 0.0179 mm. FIG. 5 is a schematic of an exemplary OTC imaging geometry, according to an embodiment of the invention. As the optical fiber rotates, N scanlines per frame are obtained with a transverse resolution of $\Delta x$ and an axial resolution of $\Delta z$. FIG. 6 is a table of other physical quantities that characterize OTC, along with exemplary values. The experimental scans can be stored as multi-frame TIFF images, each containing a 2D image with 16 bits per sample. An exemplary TIFF image frame obtained from an OCT scan is pictured in FIG. 7. Each frame shows the intensity of the reflected light for all the scan lines within one rotation of the scanning probe. If the first samples in each scan line that contain the reflections from the optical fiber and the inner and outer surface of the sleeve guiding the fiber are discarded, one spot with high intensity that indicates the position of the ear surface from which light is being reflected can be found in each scan line.

A 3D reconstruction can be performed by extracting the positions of these spots and creating a 3D point cloud from them. Before selecting the maximum intensity of each scan line, the noisy data set is smoothed by using a symmetric Gaussian lowpass filter of size 5 and standard deviation σ=2. In the following description, the OCT scan data is represented as a two-dimensional array s(i,j), where i is the scan line number and j is a specific measuring point on a scan line. The separation into frames can optionally be discarded, thus the scan lines of all frames can be appended, indexing them with just one variable i. If the separation into frames is to be retained, the data can be stored in a three-dimensional array using a third index k to identify the frame number. For each pixel position j on a stored scan line, the distance from the fiber can be computed simply as $$d(j) = d_0 + \frac{j}{d_s}, \qquad (1)$$

where $d_0$ is the offset from the center of the fiber and $d_s$ is the sampling rate. Exemplary units for the sampling rate are pixels per millimeter. According to an embodiment of the invention, for each intensity value that is above a predefined threshold (an exemplary, non-limiting value is 4000), the distance from the fiber is calculated according to this equation and stored in an intermediate object file. This data file is imported by the reconstruction algorithm and used for the computation of the 3D surface point cloud.

3D Reconstruction

Figure 8:
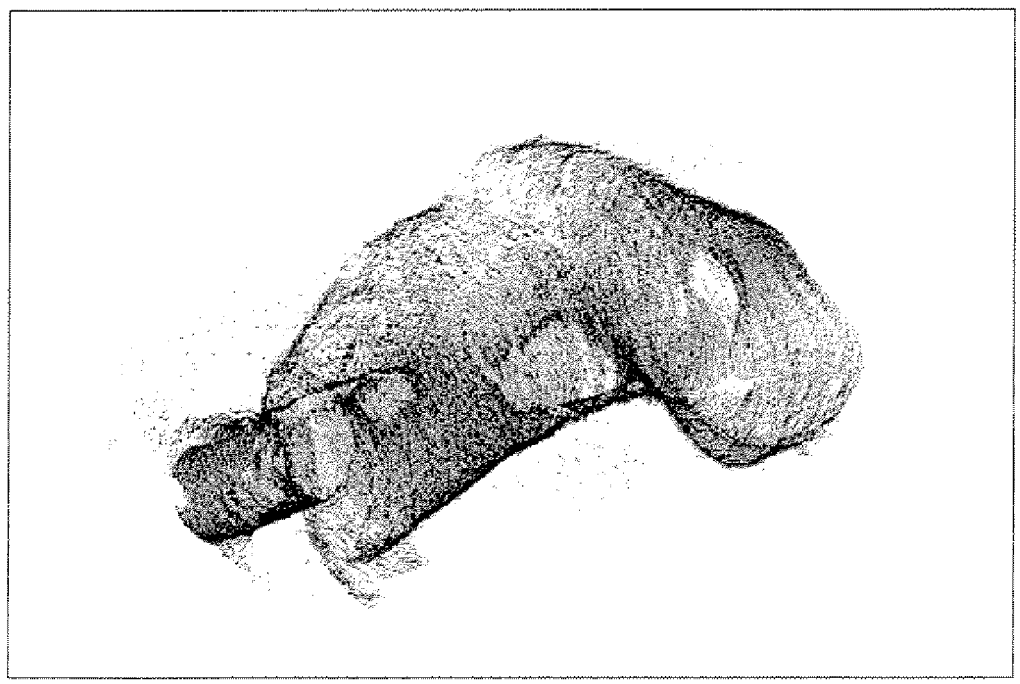
FIG. 8 depicts a reconstructed 3D point cloud obtained from an OCT scan of an ear model, according to an embodiment of the invention.

Assuming that the fiber is a straight line parallel to the x-axis of a Euclidian coordinate frame that does not deform during the scanning process, the position in space of each measured value s(i,j) can be calculated as follows:

$$t = i \cdot \frac{v}{f},$$

$$\alpha = i \cdot \frac{\omega}{f},$$

$$\vec{p}(i, j) = \vec{p}_0 + \begin{pmatrix} t \\ d(j)\sin(\alpha) \\ d(j)\cos(\alpha) \end{pmatrix},$$

where $\vec{p}_0$ is the position in space where the scan starts, v is the probe speed, f is the line sampling frequency, ω is the angular speed of the probe, t is the position on the fiber glass and α is the scan line angle, both for a specific scanline index i. Exemplary line sampling frequency units are lines per second. FIG. 8 depicts a reconstructed 3D point cloud obtained from an OCT scan of an ear model that was scanned by using a straight sleeve guiding the optical fiber.

However, the outer ear cannot be adequately scanned by a strait guide due to the limited range of the OCT system. According to an embodiment of the invention, one possible solution is the use of a curved sleeve guiding the fiber, such as the exemplary guide depicted in FIG. 1, so that the scan path is more similar to the ear shape. Then, a generalization of the reconstruction method can incorporate the curved path function. For the straight path used up to now, the 3D position $\vec{p}(i, j)$ denotes a line perpendicular to the optical fiber for any fixed i. For altered values of i those lines are placed on a spiral around the sleeve in which the optical fiber is pulled back with the probe speed. Hence, according to an embodiment of the invention, the reconstruction equation can be generalized to:

$$\vec{p}(i,j) = \vec{p}_0 + \vec{c}(t) + d(j)(\sin(\alpha)\vec{u} + \cos(\alpha)\vec{v}), \qquad (2)$$

where $\vec{c}(t)$ represents the curved path of the sleeve. Now the optical fiber can be pulled backward on an arbitrary path expressed by the parametric curve function $\vec{c}(t)$. Exemplary, non-limiting functions can be piece-wise defined from line or curved segments or as free-form curves. The vectors $\vec{u}$ and $\vec{v}$ are two unit vectors perpendicular to each other, defining a 2D coordinate frame in the plane perpendicular to the curve so that the scan line can be rotated within that plane. Note that $\vec{u}$ and $\vec{v}$ should be consistent throughout the whole curve path, i.e. that they do not twist around the curve function. According to an embodiment of the invention, one way to achieve that is to define a vector $\vec{w}$ which is not perpendicular to the curve $\vec{c}(t)$ at any time. Then, according to an embodiment of the invention, the tangent $$\vec{t} = \frac{d}{dt}\vec{c}(t)$$

can be used to derive the plane coordinate system:

$$\vec{u} = \frac{\vec{t} \times \vec{w}}{|\vec{t} \times \vec{w}|},$$

$$\vec{v} = \vec{t} \times \vec{u},$$

where "x" represents the vector product.

For a curved scan path, there are two parameters that affect the way the data is compounded in 3D space for the reconstruction. These two parameters are the position t on the scan path, where the OCT scan starts, and the corresponding rotation angle $\alpha \in [0, 2\pi]$ of the fiber. These parameters are not contained in the acquired OCT data set. An additional issue arises from manufacturing tolerances of the curved sleeve. If the actual scan path is different from the assumed scan path, 3D reconstruction will be inaccurate. The information needed for reconstruction includes the following.

(1) The analytical equation of the guide is known and the manufactured guide conforms accurately to the prescribed shape.

(2) The position of the scanning head within the guide and the direction in which the light is emitted and reflected is known throughout the scanning process.

The aim is to reconstruct the inner and outer part of the ear with an accuracy of 0.1 mm per point.

Error Evaluation

To evaluate the accuracy of the reconstructed data set in an embodiment of the invention, one needs to assess the error between the reconstructed 3D point cloud and a model object's data set. Some of the ear models provided for testing the OCT scans also have 3D CT scans that can be regarded as model data sets. In order to compare the reconstructed data set and the model data set, their coordinate systems need to be matched. Therefore a 3D rigid transformation needs to be performed before the error between the two data sets can be computed.

Since the two point clouds are not acquired using a common coordinate system, a rigid transformation in 3D should be established in order to compare the two data sets. There are several ways to describe a rigid transformation. According to an embodiment of the invention, a 3D rigid transformation has 6 degrees of freedom, three rotational angles $\theta_x$, $\theta_y$, $\theta_z$, and three translational values $t_x$, $t_y$, $t_z$, and thus is fully described by a six parameter vector $[t_x, t_y, t_z, \theta_x, \theta_y, \theta_z]^T$ This parameterization is known as the Euler Angle Representation. Using homogenous coordinates, a rigid transformation becomes a linear mapping:

$$\begin{pmatrix} x_{trans} \\ y_{trans} \\ z_{trans} \\ 1 \end{pmatrix} = T_{trans} \cdot \begin{pmatrix} x \\ y \\ z \\ 1 \end{pmatrix}$$

The transformation matrix $T_{trans}$ can be represented by a 4%4 matrix comprising a 3%3 rotation matrix and a 3%1 translation vector:

$$T_{trans} = T(t_x, t_y, t_z) \cdot R_z(\theta_z) \cdot R_y(\theta_y) \cdot R_x(\theta_x)$$

$$= \begin{pmatrix} 1 & 0 & 0 & t_x \\ 0 & 1 & 0 & t_y \\ 0 & 0 & 1 & t_z \\ 0 & 0 & 0 & 1 \end{pmatrix} \cdot \begin{pmatrix} c_z & -s_z & 0 & 0 \\ s_z & c_z & 0 & 0 \\ 0 & 0 & 1 & 0 \\ 0 & 0 & 0 & 1 \end{pmatrix} \cdot \begin{pmatrix} c_y & 0 & s_y & 0 \\ 0 & 1 & 0 & 0 \\ -s_y & 0 & c_y & 0 \\ 0 & 0 & 0 & 1 \end{pmatrix} \cdot$$

$$\begin{pmatrix} 1 & 0 & 0 & 0 \\ 0 & c_x & -s_x & 0 \\ 0 & s_x & c_x & 0 \\ 0 & 0 & 0 & 1 \end{pmatrix}$$

$$= \begin{pmatrix} c_y c_z & (s_x s_y c_z - c_x s_z) & (c_x s_y c_z + s_x s_z) & t_x \\ c_y s_x & (s_x s_y s_z + c_x c_z) & (c_x s_y s_z - s_x c_z) & t_y \\ -s_y & s_x c_y & c_x c_y & t_z \\ 0 & 0 & 0 & 1 \end{pmatrix},$$

where $s_x=\sin(\theta_x)$, $c_x=\cos(\theta_x)$, $s_y=\sin(\theta_y)$, $c_y=\cos(\theta_y)$, $s_z=\sin(\theta_z)$, $c_z=\cos(\theta_z)$. The 4th row is filled with [0, 0, 0, 1] as there is not a perspective part in this rigid transformation.

It should be noted that the Euler Angle Representation is not unique, since matrix multiplication is not commutative, i.e. $R_x R_y R_z \gamma R_y R_x R_z$, and the Euler angles suffer from the Gimbel lock phenomenon: when object points are first rotated around the x-axis by $$\frac{\pi}{2}$$

and then around the y-axis by $$-\frac{\pi}{2},$$

the angles $\theta_x$ and $\theta_z$ rotate around the same axis and thus the rotations around the x- and z-axis, respectively, can no longer be distinguished. However, the Euler Angle Representation is sufficient as a transformation that includes such critical angles will not be used.

According to an embodiment of the invention, the error between the reconstructed data set and the model data set can be measured by computing the sum of the distances of each point in the two data sets. A fast method to look up the distance from any point in space to the model data set is desired. According to an embodiment of the invention, a distance volume from the model data set can be constructed. This can be done offline without any time constraints and yields a representation of the model with very high precision.

Figure 9:
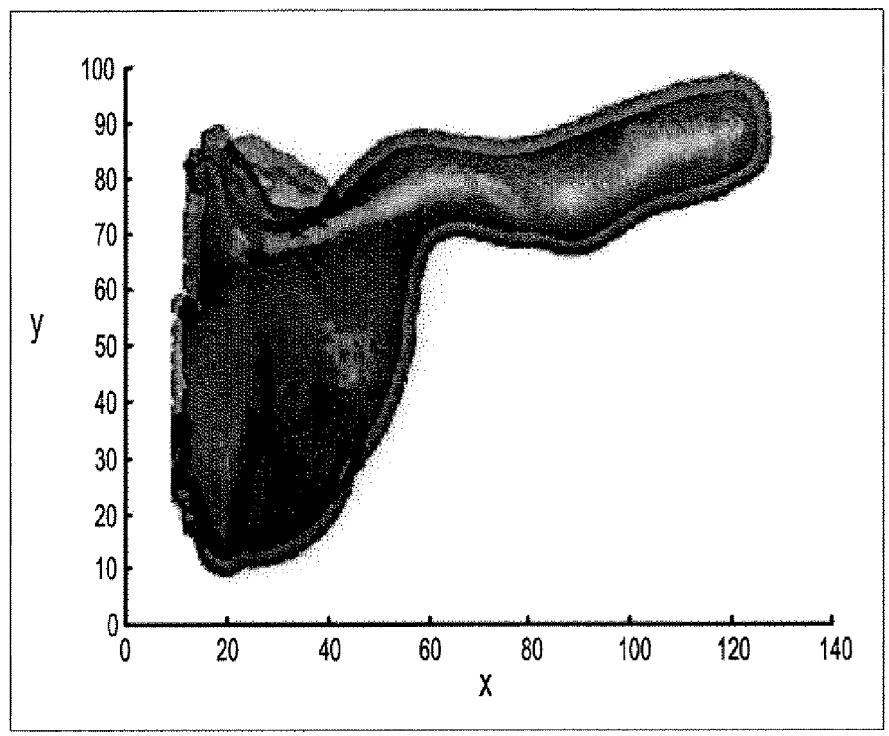
FIG. 9 depicts an isosurfare of a particular distance value in an unsigned distance volume of a 3D CT ear scan, according to an embodiment of the invention.

According to an embodiment of the invention, the distance to the model is computed by using kd-trees so that for each voxel in the distance volume the closest point in the model data set is determined. This method does not need a triangulated surface representation of an unorganized data set, which is difficult to compute. A drawback, however, is that the distances are not signed and the distance values are not zero on the model surface since there is always some distance to the sampling points. The computed unsigned distance volume of a 3D CT ear scan can be visualized by creating an isosurface from a particular distance value, as depicted in FIG. 9.

The error between the reconstructed and the model data set can then be calculated by looking up the distances in the previously computed distance volume using trilinear interpolation, adding them up and dividing through by the number of reconstructed points.

Calibration

As stated above, in order to be able to reconstruct the ear canal and concha from OCT scan data, one must ensure that the guide is manufactured as accurately as possible so that the analytical equation of the scan path conforms with the real shape of the guide, and one must define as precisely as possible the position on the path where the scanning process is started and the direction in which light is sent out first. For determining the starting position and direction of the scanning process, a calibration guide with special markings on it can be devised so that the starting point and angle in each scan generated with this guide can be identified. Exemplary markings are laser etched into the surface of the guide, forming dents on the surface. Reflections from these etched dents can be easily distinguished from surface reflections from the guide. As the markings of the calibration object show up in the scan data, the starting point and angle of the calibration scan can be easily extracted. Knowing the starting point and angle of the calibration scan, the marker positions on the guide that also come up in the scan data can be computed. The calibrated guide can then be used for scanning ear surfaces, since the known positions of the markers can help to extract the starting position and direction of the probe head during each scanning process.

Figure 10:
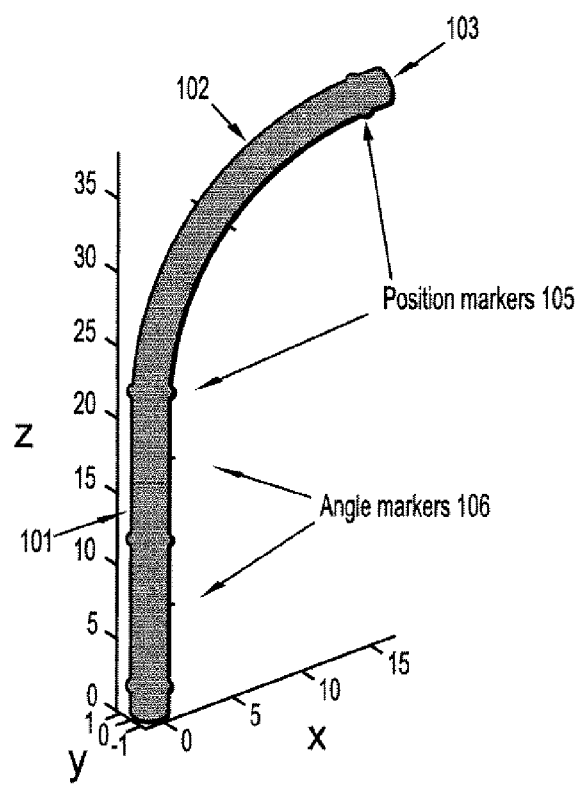
FIG. 10 depicts an exemplary, non-limiting curved calibration guide in accordance with an embodiment of the invention.

An exemplary, non-limiting curved calibration guide in accordance with an embodiment of the invention is depicted in FIG. 10, and includes two kinds of markings on it. Position markers 105 are placed as rings with certain distances from one another. Angle markers 106 are placed on the side of the guide. The guide should be manufactured as accurately as possible. In order to avoid inaccuracies during the manufacturing process the centerline of the guide lies in only one plane. A first portion 101 of the guide is straight up to a length of 22 mm, followed by a second portion 102 in the shape of a quarter circle with a radius of 15 mm, and is then a third portion 103 is straight again for a length of 2 mm. The whole length of the guide adds up to 47.55 mm and the outer wall of the guide has a radius of 1.588 mm. In accordance with an alternative embodiment of the invention, three crosses can be laser marked on the guide at random instead of being placed as shown in FIG. 10.

An exemplary guide is manufactured from polycarbonate because it can be heat shaped and laser marked with precision. Laser markings on other tubing materials would not yield the fine crisp lines that are needed. The parametric curve function $\vec{c}(t)$ for the scan path along which the scanning head is pulled back within the guide can be described in three parts:

$$\vec{c}(t) =
\begin{cases}
\begin{pmatrix} 0 \\ 0 \\ t \end{pmatrix} & \text{if } t[22 \\
\begin{pmatrix} 15 - (15 \cdot \cos\theta) \\ 0 \\ 22 + (22 \cdot \sin\theta) \end{pmatrix} & \text{if } t > 22 \text{ and } t[(22 + 2\pi 15/4) \\
\begin{pmatrix} 15 + \left(t - 22 - \dfrac{2\pi 15}{4}\right) \\ 0 \\ 22 + 15 \end{pmatrix} & \text{if } t > (22 + 2\pi 15/4) \text{ and } t[(22 + 2\pi 15/4 + 2)
\end{cases}$$

where t is the distance from the beginning of the path to the current point on the path (in mm) and θ is the angle between the line connecting the center of the quarter circle with the point t and the x-axis. As the parameterization of the scan path is needed for the reconstruction procedure, it was integrated in the reconstruction algorithm explained above.

Figure 11:
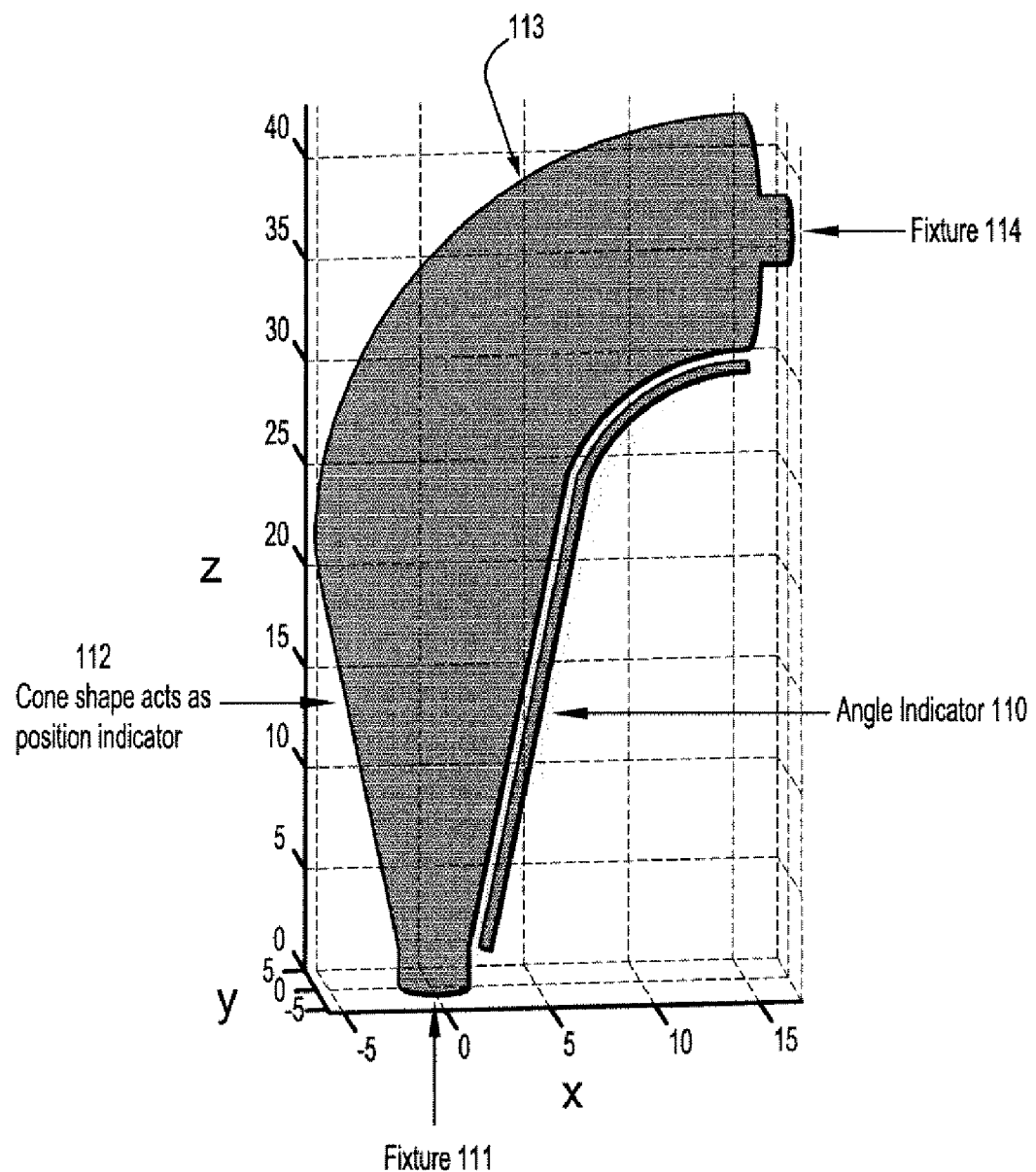
FIG. 11 depicts an exemplary, non-limiting calibration object in accordance with an embodiment of the invention.

In accordance with an embodiment of the invention, a calibration object was devised as well. An exemplary, non-limiting calibration object is depicted in FIG. 11, and includes two kinds of markings on it as well. The cone shape 112 encodes the position of the scanning head, and there is a groove 10 with a depth of 1 mm on the side that indicates the zero angle. This should be taken into account when the unit vectors $\vec{u}$ and $\vec{v}$ that define the plane perpendicular to the scan path are computed and the direction in which light is sent out for an angle α=0.0 degrees is determined. There are also two fixtures 111, 114 on the calibration object that can be used to reproducibly position the guide within the object shell. The two fixtures of the calibration object have a length of 2 mm and a radius of 1.588 mm, the same width as the calibration guide. The fixture 111 beginning at z=0 is referred to as section 1, and the fixture 114 at the end of the calibration object is referred to as section 4. The cone-shaped part 112 has a length of 20 mm and is referred to as section 2. The maximum radius of 5.588 mm is reached at the total length of 22 mm. Then the radius stays constant while the calibration object forms a quarter circle in the same way as the guide. This part 113 is referred to as section 3. An exemplary, non-limiting calibration object was manufactured from two half shells milled of aluminum.

An exemplary, non-limiting calibration method in accordance with an embodiment of the invention includes at least one calibration scan using the laser marked calibration guide. The optical fiber was pulled backward on the scan path expressed by the parametric curve function $\vec{c}(t)$ defined above. In order to reconstruct the calibration object the position on the guide where the OCT scan starts and the corresponding rotation angle of the fiber have to be extracted out of the calibration scan data. For the following computations the separation of the OCT scan data into frames was retained, indexing the frame number with the variable $n_F$ and the scan line number in each frame with the variable $n_S$. The scan line number can take values from 1 to 256 as each frame contains 256 scan lines. The frame number depends on the scan data.

To determine the starting point and starting angle for the calibration scan, one examines the scans and extracts the frame and scan line number that indicate a certain position of the scanning head within the calibration cavity. With the guide being attached to the calibration object, one also knows the position of the probe head within the calibration guide.

As the scanning process for the calibration object was started outside the calibration guide, the first step is to specify that position in the scan data where the guide shows up for the first time. But since the guide is longer than required by specification, this position in the scan data does not match the starting point t=0.0 mm of the parametric curve function $\vec{c}(t)$. Therefore, instead of searching for the frame in which the guide comes up for the first time, one can look for the frame in which the cone-shaped part of the calibration object begins. This frame can be selected very precisely because it is the one in which the groove appears for the first time.

Figure 13:
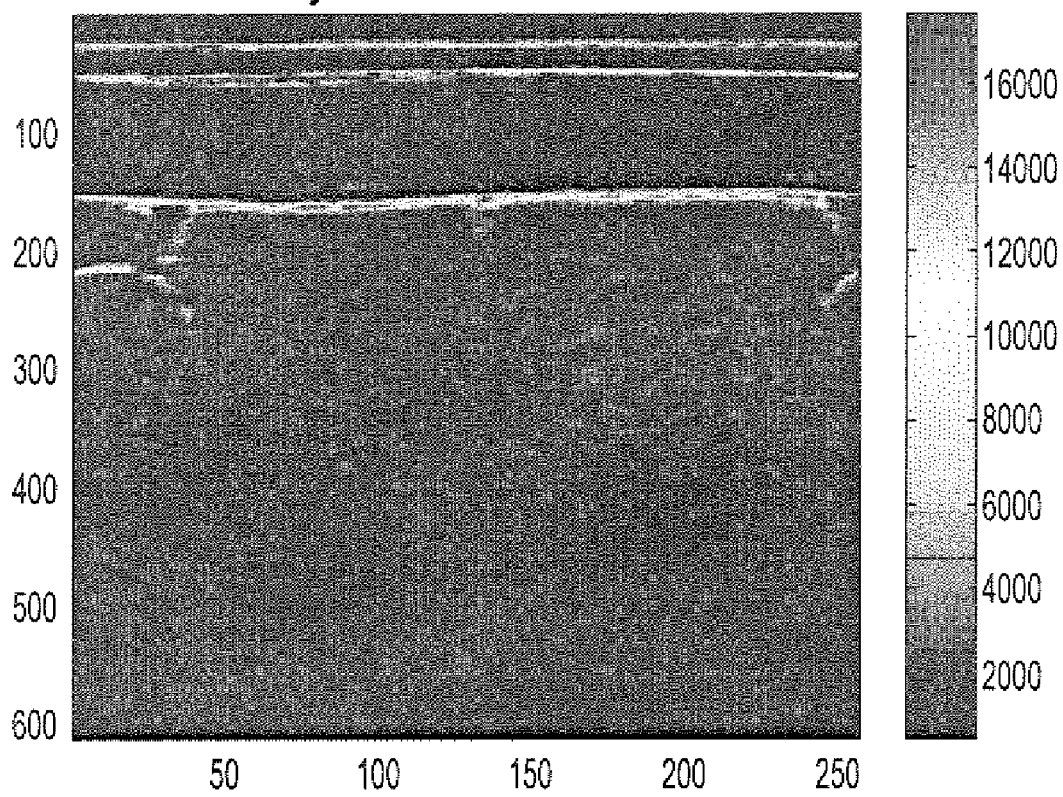
FIG. 13 depicts a second frame that contains light reflections from the cone-shaped part of the calibration object, according to an embodiment of the invention.

FIG. 12(a) depicts the last frame in which light reflections from section 1 of the calibration object can be observed, and FIG. 12(b) depicts the first frame in which light reflections from the cone-shaped surface can be perceived. The groove can be seen on the left side in FIG. 12(b). As there is no indication which scan line contains the first light reflection from the cone-shaped part, the beginning of this section can be determined with an accuracy of 0.08 mm which corresponds to 256 times the resolution of 3.125%10$^{-4}$ mm along the scan path. Hence, the center line of the groove that indicates the zero angle can be assumed to be that line where light has been first backscattered from the cone-shaped part of the calibration object. FIG. 13 depicts a second frame that contains light reflections from the cone-shaped part of the calibration object. Since the groove stretches across 30 scan lines, beginning at $n_S$=0 until $n_S$=30, as shown in FIG. 13, $n_S$=15 can be selected as the center line of the groove.

In order to do the 3D reconstruction based on EQ. (2), the frame and scan line number should be computed in which the first reflection from the originally designed calibration guide with a length of 47.55 mm would have been detected. The reflection in this scan line then corresponds to the reflection of light that has been sent out at the position $\vec{c}$(t=0.0). The resolution of the scan path Δt can be defined as $$\Delta t = \frac{v}{f},$$

where v is the probe speed, f is the line sampling density, and the number of scan lines needed for covering the distance t along the scan path, $N_S$, can be defined as $$N_S = \frac{t}{\Delta t}.$$

Assuming a probe speed of 0.5 mm/s, 25 frames each containing 256 scan lines are needed to scan the straight part of 2 mm. The calculation can be performed easily by subtracting 25 frames from the frame and scan line number that indicate the beginning of section 2 of the calibration object. As the center line of the groove is assumed to be the scan line that indicates the first reflection from the cone-shaped part and exactly 25 frames are needed to scan section 1 of the calibration object, the scanning process starts at frame 76 and scan line 15 corresponding to a starting position of t=0.0 mm and an angle of α=0.0 degrees.

The calibration object can now be reconstructed as explained above. Before searching for the maximum intensity "bright spots" in each scan line, the reflections from the optical fiber and the inner and outer surface of the sleeve guiding the fiber should be eliminated. However, the reflection spots from the outer surface of the guide are not cut off in those frames that contain the reflections from the fixtures of the calibration object. As the fixtures have the same radius as the guide, the light reflections from the outer surface of the guide and the calibration object coincide. If the light reflections from the guide were cut off in these frames, one would also loose the information about the calibration object. Therefore the reflections from the outer surface of the guide are not eliminated in those frames in which the reflections from the two fixtures appear, whereas they are truncated in all the other frames.

Figures 14, 18:
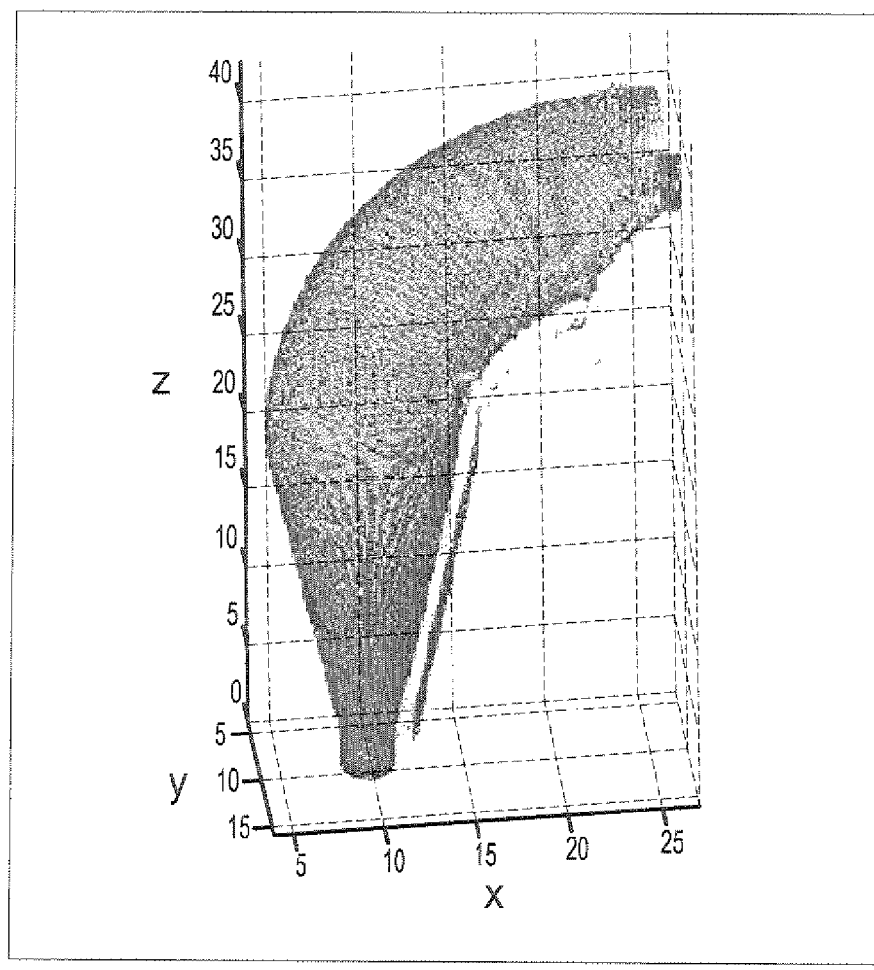
FIG. 14 depicts an exemplary a distance volume representation of the model data set, illustrated as a 3D point cloud, according to an embodiment of the invention.
FIG. 18 is a table of exemplary computed starting parameters, according to an embodiment of the invention.

The distances corresponding to the "bright spots" can be computed from EQ. (1). The starting parameters can be computed, the frame and scan line number in which the reflection of light sent out at the position $\vec{c}(t=0.0)$ shows up can be extracted, and the marker positions on the guide can be calculated as explained below. The calibration object reconstructed with $\alpha_{start}=0.0$ degrees and $t=0.0$ mm is depicted in FIG. 14.

Figures 15, 17:
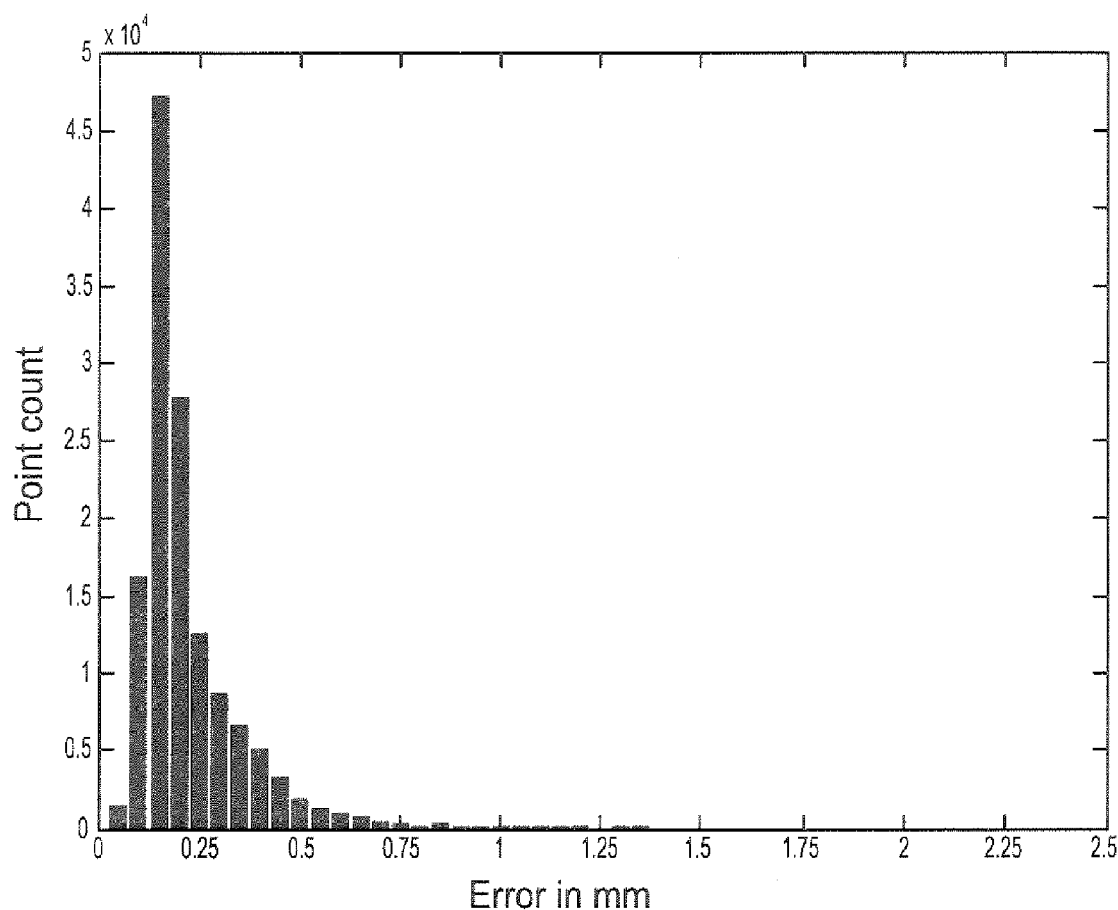
FIG. 15 depicts a histogram of the error per point between the reconstructed and model data sets, according to an embodiment of the invention.
FIG. 17 is a table of exemplary computed marker positions for two calibration data sets, according to an embodiment of the invention.

For evaluating the precision of the reconstructed calibration object, a distance volume representation of the model data set, as described above in connection with error evaluation, has to be computed. FIG. 14 depicts an exemplary a distance volume representation of the model data set, illustrated as a 3D point cloud. The distance volume computation can be performed offline. This time the position of the guide within the shell is known quite exactly, since the guide was attached to the fixtures on the calibration object during the scanning process. By matching the two coordinate systems of the reconstructed data set and the distance volume representation, the error between the two data sets can be calculated as explained above. The error between the reconstructed 3D point cloud and the model data set averages out at 0.2418 mm per point. A histogram of the error per point between the reconstructed and model data sets is shown in FIG. 15. The points with the largest errors are accumulated in an area around the border between section 2 and section 3 of the calibration object and the border between section 3 to section 4. They are also gathered at the inner part of section 3 where the groove cannot be detected. At this part the reflections from the groove are too low to be extracted out of the scan data. It can be assumed that the guide was twisted by attaching it to the fixture. That means that this part of the parametric curve function $\vec{c}(t)$ needed for reconstruction differs from the actual scan path along which the optical fiber was tracked during the scanning process, which in turn leads to an inaccurate reconstruction of the calibration object. However, the achieved overall accuracy of the reconstructed calibration object is satisfactory.

As mentioned before, three crosses are laser marked on the guide. To compute the marker positions on the guide, the frame and scan line number in which the markers show up need to be extracted from the calibration scan data. FIGS. 16(a)-(e) show the appearance of the laser marked crosses in the calibration scan. Each marker appears in several frames, mostly in five or six frames as shown in the figures. The middle frame, FIG. 16(c), in which the marker can be identified best, and the center scan line are taken for the computation of the marker position on the guide. The marker positions on the guide can be calculated by using the following equations:

$$\alpha_{marker}[\text{rad}] = \begin{cases} 2\pi - (n_{s_{\alpha=0}} - n_{s_{marker}}) \cdot d_\alpha, & \text{if } n_{s_{\alpha=0}} > n_{s_{marker}} \\ (n_{s_{marker}} - n_{s_{\alpha=0}}) \cdot d_\alpha & \text{if } n_{s_{\alpha=0}} \le n_{s_{marker}} \end{cases} \quad (3)$$

$$t_{marker}[\text{mm}] = ((n_{F_{marker}} - n_{F_{start}}) \cdot N + (n_{s_{marker}} - n_{s_{start}})) \cdot \Delta t, \quad (4)$$

where $n_S$ is a line number, $n_F$ is a frame number, $d_\alpha$ is the angular increment, N is the number of lines per frame, and $\Delta t$ is the resolution along the scan path. In particular, $n_{S_{\alpha=0}}$ defines a start value in a pre-defined relationship with the groove marker, while $n_{F_{start}}$ and $n_{S_{start}}$ represent predefined start values that are a known distance from first marker, or optionally the first marker itself. Note that the units (rad, m) indicated in the above equations are exemplary, and other systems of units can be used without limitation. Exemplary computed marker positions for two calibration data sets are listed in the table depicted in FIG. 17. The marker positions extracted from the two calibration data sets differ by about 0.08 mm to about 0.16 mm and by about 0.0245 rad to about 0.049 rad. The deviations of 0.08 mm and 0.16 mm correspond to an inaccuracy of one and two frames and the variation of 0.0245 rad and 0.049 rad to an inaccuracy of one and two scan lines. This means that the extraction of the frame and scan line number for either the beginning of section 2 or the marker positions, or possibly both, can be performed with the aforementioned accuracy.

Reconstruction of Ear Scan Data

After the calibration stage the calibrated guide can now be used for scanning ears. Before performing 3D reconstruction, one needs to determine starting position and angle of the scanning head for each scanning process, by examining the scan data and determining as exactly as possible the frame and scan line number in which the three laser marked crosses show up.

The starting position and angle corresponding to each marker position can be easily computed as from the following exemplary definitions for marker1:

$$\alpha_{start1} = \quad (5)$$
$$\begin{cases} \alpha_{marker1} - n_{s_{marker1}} \cdot d_\alpha, & \text{if } \alpha_{marker1} - n_{s_{marker1}} \cdot d_\alpha \ge 0, \\ 2\pi + \alpha_{marker1} - n_{s_{marker1}} \cdot d_\alpha, & \text{if } \alpha_{marker1} - n_{s_{marker1}} \cdot d_\alpha < 0, \end{cases}$$

$$t_{start1} = t_{marker1} - ((n_{F_{marker1}} - 1) \cdot N + n_{s_{marker1}}) \cdot \Delta t. \quad (6)$$

Once the scan has moved past the markers, one can obtain the marker information to position/align all the imaging data correctly in space in the portion of the guide where the guide has been parameterized from the calibration. In an optimal case, starting position and angle should be the same for each of the three calculations. But as frame and scan line number of the marker positions cannot be determined exactly, the three calculations do not yield the same result. Exemplary computed starting parameters from three scans are shown in the table of FIG. 18. The values for the starting point vary by approximately 0.5 mm, and the starting angle differs in an interval of about 35 degrees, as shown in the table. These deviations can be traced back to the fact that the guide markers are crosses for which exact positions cannot be exactly determined. Since the markers appear in six or seven scans, a deviation of 0.5 mm corresponding to about four rotations and thus four frames is not surprising, and since the markers stretch across almost 30 scan lines corresponding to a range of about 40 degrees, an angle deviation of 35 degrees is also comprehensible. Because of the mentioned variations, the final values can be computed by averaging the three former values:

$$\alpha_{start} = \frac{1}{3}(\alpha_{start1} + \alpha_{start2} + \alpha_{start3}), \quad (7)$$

$$t_{start} = \frac{1}{3}(t_{start1} + t_{start2} + t_{start3}).$$

The equations above are used when the scan is started at the straight part of the guide. If the scanning process is started at the other end of the guide, the equations need to be changed, which is straightforward transformation.

Figure 19:
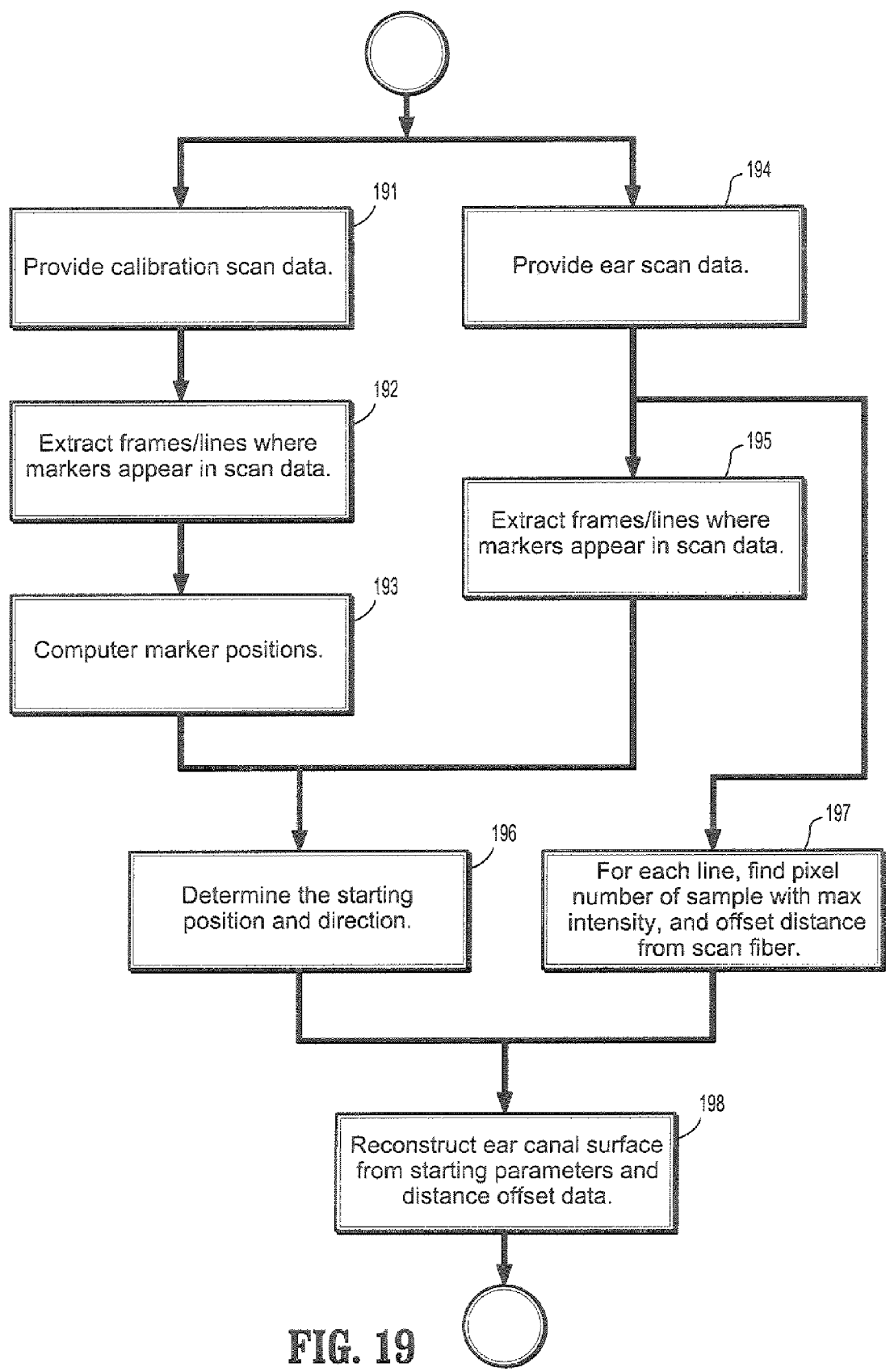
FIG. 19 is a flow chart of an ear reconstruction process according to an embodiment of the invention.

A flow chart of an ear reconstruction process according to an embodiment of the invention is shown in FIG. 19. First, the guide used for scanning ears is calibrated. The calibration object is scanned with an OCT scanner to provide a set of calibration scan data at step 191. The frames and scan lines of OCT scan data form a 3D data set whose values are interference intensities. At step 192, those frames and scan lines where the markers on the guide appear are extracted, from which the marker positions on the guide can be computed according to EQS. (3) and (4) at step 193. As the markers appear in the ear scan data, this information can be used to compute the starting point and angle for any ear scan that has been recorded utilizing the calibrated guide. The calibration marker positions can be saved to a file for future use. Note that for reconstructing the calibration object, the starting parameters can be determined from the frame and scan line where section 2 of the calibration object, which includes the groove, begins.

The ear is scanned with an OCT scanner to provide a set of ear scan data at step 194. This data also forms a 3D data set and can be smoothed with a low pass filter as described above. At step 195, those frames and scan lines where the markers on the guide appear are extracted. Comparison of the ear scan marker positions with the calibration scan marker positions enables the calculation of the starting parameters at step 196, according to EQS. (5), (6), and (7). At step 197, the sample data for each line and each frame are examined to find the pixel number of the sample with the maximum intensity. The distance offset of the maximum intensity pixel is determined from EQ. (1). Note that the beginning samples on each scan line, which correspond to reflections from the guide, can be discarded for this step. Then, at step 198, the ear surface is reconstructed from the distance offset data using EQ. (2), using the starting position and direction provided from step 196.

Evaluation of Ear Scan Data

Figure 20:
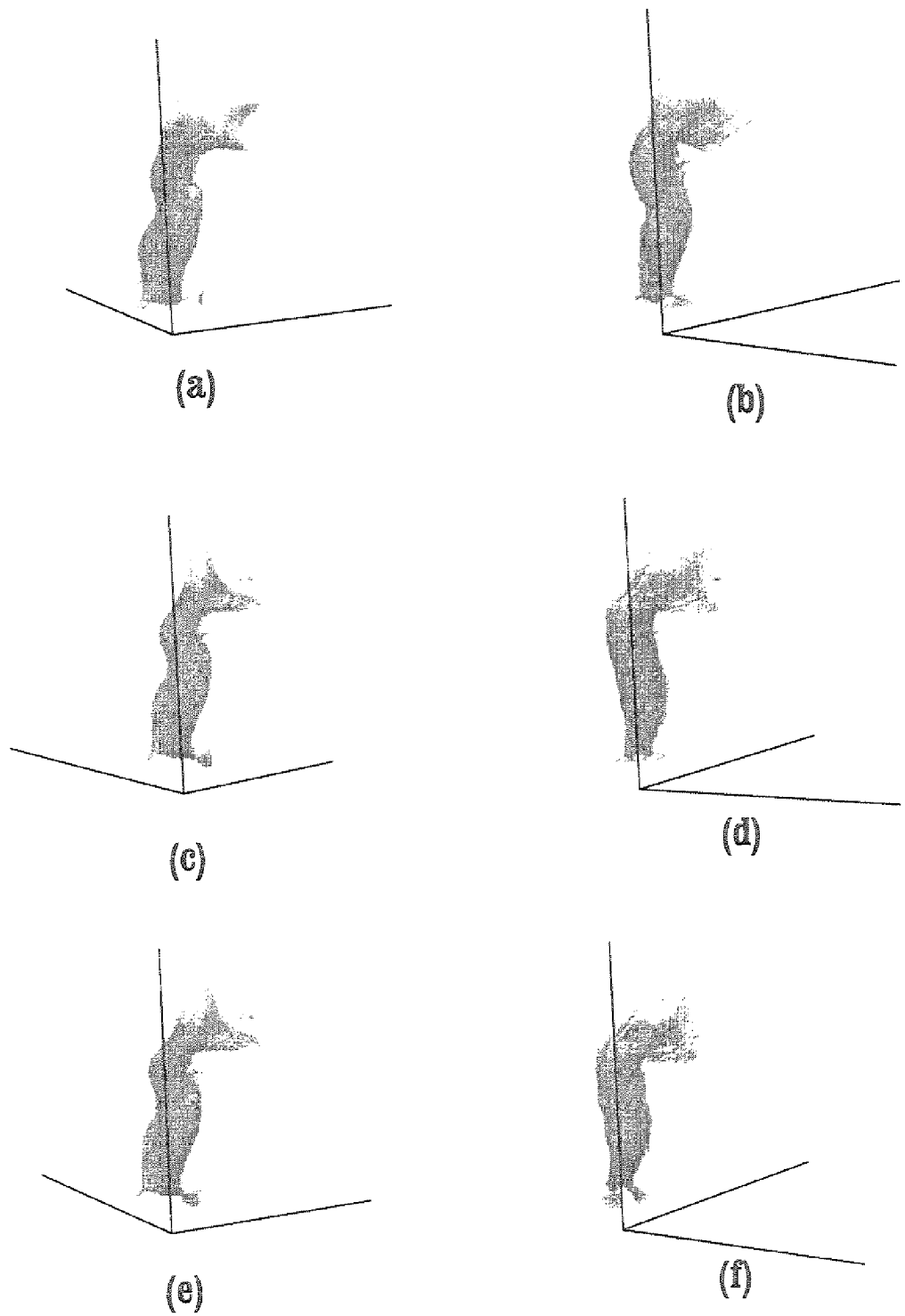
FIGS. 20(a)-(f) depict reconstruction results for the ear canal and concha, according to an embodiment of the invention.
Figure 21:
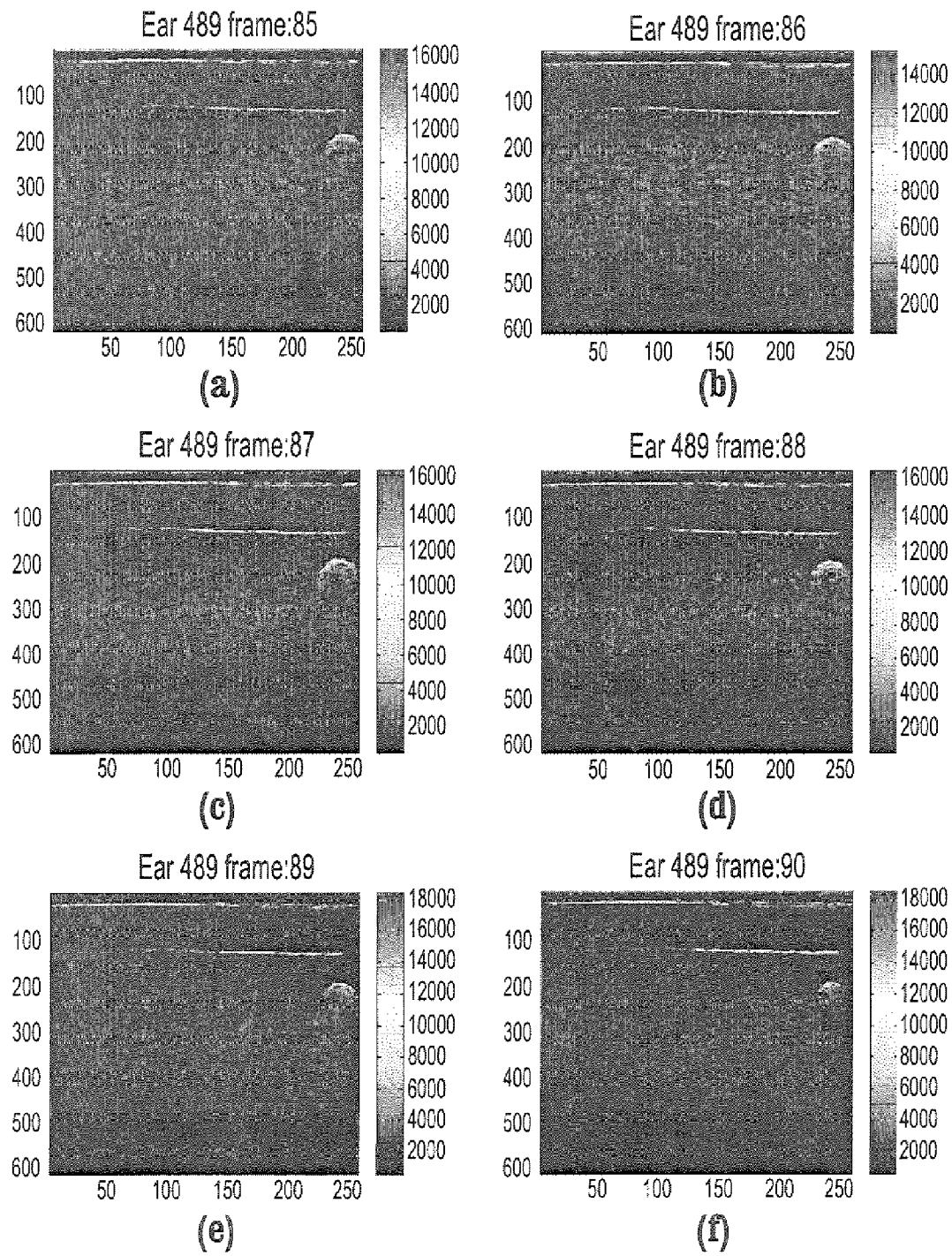
FIGS. 21(a)-(f) depict frames in which light reflections from the ear concha were expected, according to an embodiment of the invention.

Experiments of ear reconstruction methods according to an embodiment of the invention were performed using a model ear manufactured from silicon. FIGS. 20(a)-(f) depict reconstruction results for the ear canal and concha. As it can be seen from the figures, the ear canal can be reconstructed quite well. FIG. 20(a) and FIG. 20(b) represent the same reconstructed 3D point cloud from two different points of view. FIG. 20(c), FIG. 20(d), FIG. 20(e) and FIG. 20(f) represent the reconstructed 3D point cloud from a second and third scanning process and also each of them from two different points of view. All three representations look very much the same. There are almost no openings in the surface representation of the ear canal.

FIGS. 21(a)-(f) depict frames in which light reflections from the ear concha were expected. It is more difficult to reconstruct the ear concha, as the surface of the outer ear is far from the optical fiber, and the measured intensity of light reflected from the concha is too low to be detected. When examining these frames, only a few intensity values that are higher than 4000 can be identified, as can be seen from the figure.

Figure 22:
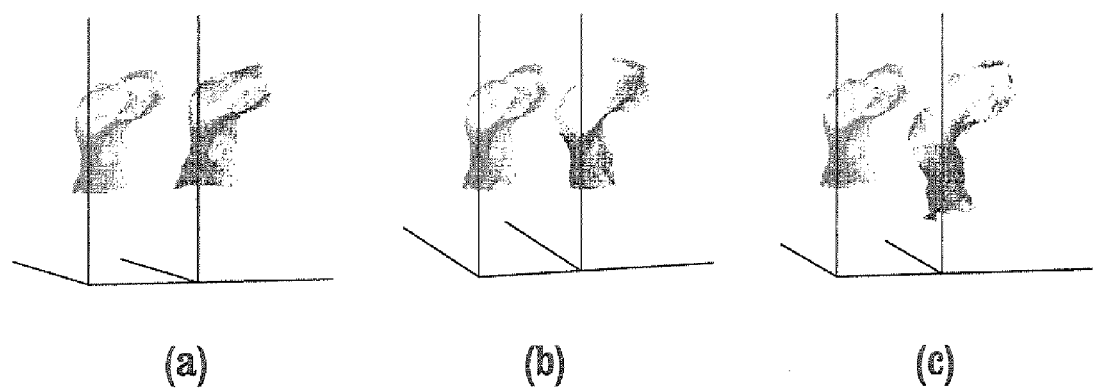
FIGS. 22(a)-(c) depict reconstruction results from four different concha scans, according to an embodiment of the invention.

In accordance with an embodiment of the invention, several OCT scans of the concha part can be used, changing the guide position for each of the scans so that different parts of the concha are scanned. The reconstructed 3D point clouds can be put together to obtain a whole 3D representation of the concha. Reconstruction results from four different concha scans are illustrated in FIGS. 22(a)-(c). The 3D point clouds displayed on the left of each group are the same, while the 3D point clouds displayed on the right are reconstructed from different scan data. The reconstructed results indicate that mostly the same part of the concha was scanned, so that putting the 3D data sets together would not lead to any further information about the concha shape. Moreover, it can be seen that sometimes light reflections from the outer surface of the guide have been extracted. That is why the first samples in each scan line should not be cut off exactly where the light reflections from the outer surface of the guide end.

Another way to scan the ear concha and obtain an interference signal of the reflected light that is strong enough to be detected would be to design a curved guide that fits the shape of the ear. One exemplary guide would have one line segment and two circle segments, so the scan path would more closely resembled the ear shape than a straight one. Another approach is to use an OCT device with a larger DOF.

The reflections from the fiber and the inner and outer surface of the guide are cut off before searching for the maximum intensity value in each scan line. However, the reflections from the guide surface do not appear at the same sample for each scan line, but vary over approximately 10 samples. Furthermore, the guide sometimes touches the ear surface during the scanning process causing reflections from the outer surface of the guide to coincide with the reflections from the ear surface. Thus, both reflections might appear as one spot with high intensity. If an insufficient number of samples are cut off in each scan line, the intensity value indicating the light reflection from the ear surface might not be detected, as it is weaker than the value indicating the reflection from the guide surface. On the other hand, if too many samples are cut off, it might happen that not only the reflection from the guide but also from the object is eliminated and can no longer be extracted. However, truncating the first samples in each scan line in order to purge the fiber and guide reflections has been sufficient for an embodiment of the invention.

It is to be understood that various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Furthermore, it is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 23:
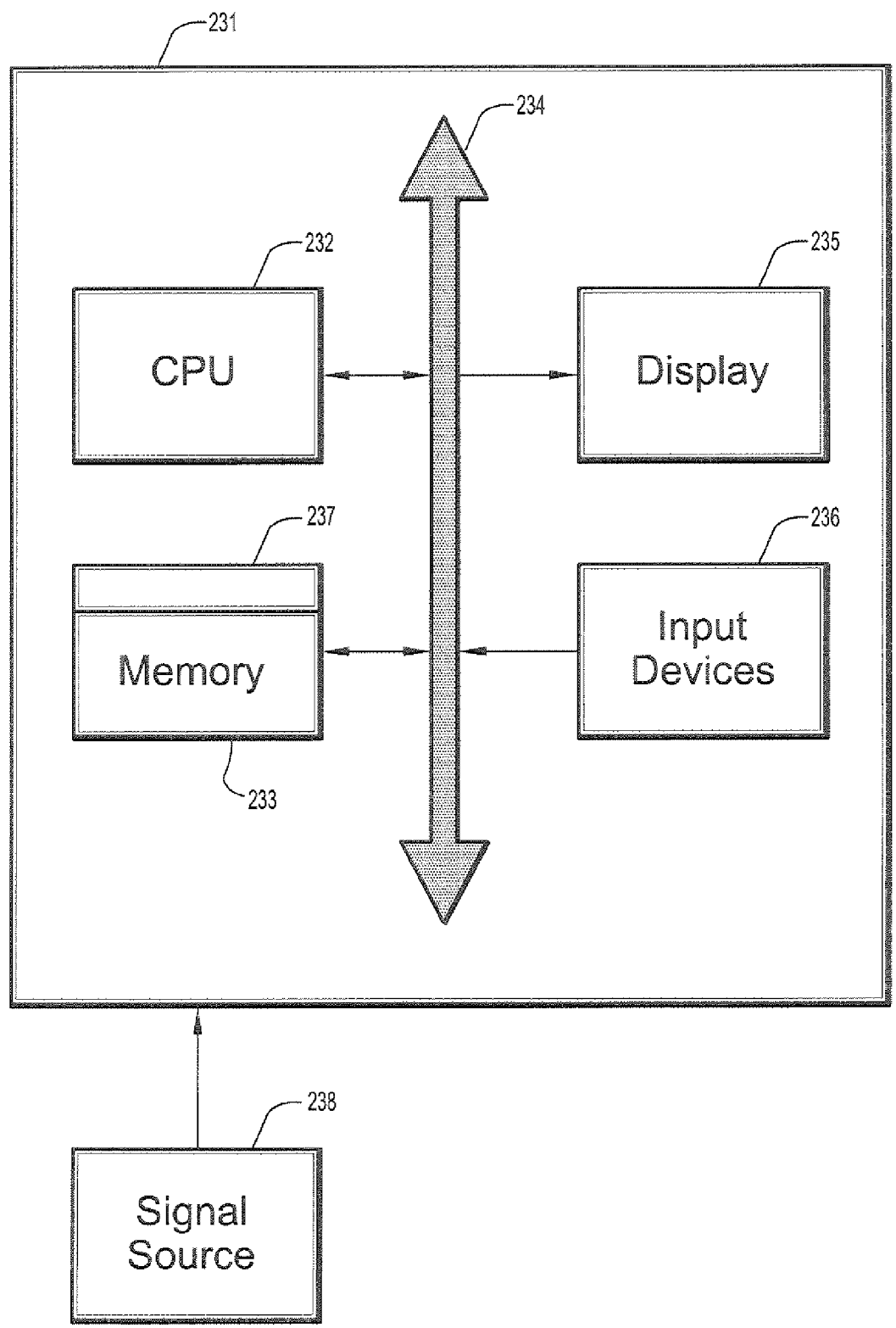
FIG. 23 is a block diagram of an exemplary computer system for implementing an ear reconstruction process according to an embodiment of the invention.

Accordingly, FIG. 23 is a block diagram of an exemplary computer system for implementing an ear reconstruction process according to an embodiment of the invention. Referring now to FIG. 23, a computer system 231 for implementing the present invention can comprise, inter alia, a central processing unit (CPU) 232, a memory 233 and an input/output (I/O) interface 234. The computer system 231 is generally coupled through the I/O interface 234 to a display 235 and various input devices 236 such as a mouse and a keyboard. The support circuits can include circuits such as cache, power supplies, clock circuits, and a communication bus. The memory 233 can include random access memory (RAM), read only memory (ROM), disk drive, tape drive, etc., or a combinations thereof. The present invention can be implemented as a routine 237 that is stored in memory 233 and executed by the CPU 232 to process the signal from the signal source 238. As such, the computer system 231 is a general purpose computer system that becomes a specific purpose computer system when executing the routine 237 of the present invention.

The computer system 231 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method for reconstructing an ear canal, comprising the steps of:
   providing a set of optical coherence tomography (OCT) scan data of an ear comprising frames and scan lines of pixels that form a 3D data set whose values are interference intensities;
   extracting frame numbers and line numbers of interference intensities corresponding to one or more markers on an OCT scan guide;
   receiving reference frame numbers and lines numbers for said one or more markers;
   determining a starting position and direction for said OCT ear scan from the ear scan marker frame and line numbers and said reference marker frame and line numbers;
   for each scan line, finding a pixel number of a maximum interference intensity value, and determining an offset distance of said pixel from said scan guide; and
   reconstructing said surface of said ear canal from said distance offset data.

2. The method of claim 1, wherein an offset distance d of a pixel j from the guide is computed from $$d(j) = d_0 + j/d_s,$$

wherein $d_0$ is an offset from the center of the guide and $d_s$ is a sampling rate.

3. The method of claim 1, wherein said ear canal surface can be reconstructed from $$\vec{p}(i,j) = \vec{p}_0 + \vec{c}(t) + d(j)(\sin(\alpha)\vec{u} + \cos(\alpha)\vec{v}),$$

wherein $\vec{p}(i,j)$ represents a scan line i perpendicular to guide, j a pixel along the scan line, $\vec{p}_0$ is a starting position in space of the scan, $\vec{c}(t)$ a curved path of the guide, t is a position on the guide corresponding to the scan line i, and $\alpha$ is a scan line angle, and $\vec{u}$ and $\vec{v}$ are two unit vectors perpendicular to each other defining a 2D coordinate frame in a plane perpendicular to the curve $\vec{c}(t)$.

4. The method of claim 3, wherein $$t = i \cdot \frac{v}{f},$$

wherein v is a scan speed of a scanning probe contained within said guide, and f is a scan line sampling frequency, and $$\alpha = i \cdot \frac{\omega}{f},$$

wherein $\omega$ is the angular speed of rotation the probe.

5. The method of claim 3, wherein said unit vectors $\vec{u}$ and $\vec{v}$ are defined by $$\vec{u} = \frac{\vec{t} \times \vec{w}}{|\vec{t} \times \vec{w}|},$$

$$\vec{v} = \vec{t} \times \vec{u},$$

wherein $\vec{w}$ is a vector that is not perpendicular to the curve $\vec{c}(t)$ at any time, and $\vec{t}$ is a tangent to the curve defined as $$\vec{t} = \frac{d}{dt}\vec{c}(t).$$

6. The method of claim 1, wherein said OCT scan data is obtained by providing an OCT scanning apparatus including, a guide containing a rotatable probe, sliding and rotating said probe in said guide, emitting near infrared light from said probe at predetermined intervals, measuring interference of reflected light with a reference signal, and saving said interference data in a computer readable storage medium.

7. The method of claim 1, comprising, for each scan line, selecting those pixels with an interference intensity value above a pre-determined threshold and determining an offset distance of said selected pixels from said scan guide.

8. The method of claim 1, comprising, prior to finding a pixel number of a maximum interference intensity value for a scan line, discarding the intensity values at the beginning of a scan line, wherein said beginning values correspond to reflections from the scan guide itself.

9. The method of claim 1, wherein said reference marker frame numbers and lines numbers were extracted from OCT scan data of a calibration object.

10. The method of claim 9, wherein extracting said reference marker frame numbers and lines numbers from OCT scan data of a calibration object comprises:
    providing a set of optical coherence tomography (OCT) scan data of a calibration object marked to indicate an angular direction of 0, said scan data comprising frames and scan lines of pixels that form a 3D data set whose values are interference intensities acquired using a calibration guide comprising one or more markers on said guide;
    extracting frame numbers and line numbers of interference intensities corresponding to said markers on said calibration guide; and determining spatial positions of said markers on said calibration guide from said frame number and said line numbers.

11. The method of claim 10, wherein said marker positions on the guide are calculated from:

$$\alpha_{marker} = \begin{cases} 2\pi - (n_{s_{\alpha=0}} - n_{s_{marker}}) \cdot d_\alpha, & \text{if } n_{s_{\alpha=0}} > n_{s_{marker}} \\ (n_{s_{marker}} - n_{s_{\alpha=0}}) \cdot d_\alpha, & \text{if } n_{s_{\alpha=0}} \le n_{s_{marker}} \end{cases}$$

$$t_{marker} = ((n_{F_{marker}} - n_{F_{start}}) \cdot N + (n_{s_{marker}} - n_{s_{start}})) \cdot \Delta t,$$

wherein $\alpha$ is an angle of rotation about said guide, $\alpha_{marker}$ is an angular direction of a marker, $t_{marker}$ is the frame number of the marker, $n_{S_{\alpha=0}}$ is a line number of a scan line at an angular direction of 0, $n_{S_{start}}$ is a starting line number, $n_{S_{marker}}$ is a line number of a scan line that contains marker interference intensity values, $n_{F_{start}}$ is a starting frame number, $n_{F_{marker}}$ is a frame number of a frame containing marker interference intensity values, $d_\alpha$ is an angular increment, N is a number of lines per frame, and $\Delta t$ is a resolution along the scan path.

12. The method of claim 1, wherein the starting position $t_{start}$ and direction $\alpha_{start}$ are computed from a marker position $t_{marker}$ and direction $\alpha_{marker}$ from $$\alpha_{start} = \begin{cases} \alpha_{marker} - n_{s_{marker}} \cdot d_\alpha & \text{if } \alpha_{marker} - n_{s_{marker}} \cdot d_\alpha \ge 0, \\ 2\pi + \alpha_{marker} - n_{s_{marker}} \cdot d_\alpha, & \text{if } \alpha_{marker} - n_{s_{marker}} \cdot d_\alpha < 0, \end{cases}$$

$$t_{start} = t_{marker} - ((n_{F_{marker}} - 1) \cdot N + n_{s_{marker}}) \cdot \Delta t,$$

wherein $n_{S_{marker}}$ is a line number of a scan line that contains marker interference intensity values, $n_{S_{marker}}$ is a frame number of a frame containing marker interference intensity values, $d_\alpha$ is an angular increment, N is a number of lines per frame, and $\Delta t$ is a resolution along the scan path.

13. A method for reconstructing an ear canal, comprising the steps of:
providing a scanning guide for an optical coherence tomography (OCT) system, said guide comprising one or more markers on its outer surface;
providing OCT scan data of a hollow calibration object acquired using said scanning guide, said scan data comprising frames and scan lines of pixels that form a 3D data set whose values are interference intensities;
extracting from said calibration object scan data reference frame numbers and line numbers of interference intensities corresponding to said one or more markers on said OCT scan guide;
providing a set of optical coherence tomography (OCT) scan data of an ear acquired using said scanning guide, said scan data comprising a 3D data set of interference intensity values;
extracting from said ear scan data frame numbers and line numbers of interference intensities corresponding to said one or more markers on said OCT scan guide; and
determining a starting position and direction for said OCT ear scan from said ear scan frame numbers and line numbers of said one or more markers and said reference frame numbers and line numbers of said one or more markers.

14. The method of claim 13, further comprising, for each scan line, finding a pixel number of a maximum interference intensity value, and determining an offset distance of said pixel from said scan guide; and reconstructing said a surface of said ear canal from said distance offset data.

15. The method of claim 13, wherein said scanning guide has at least two straight portions and a curved portion, said scanning guide adapted to containing a rotatable scanning probe.

16. The method of claim 15, wherein said calibration object comprises a first fixture at a first end, a second fixture at a second end, said fixtures adapted to securely hold said calibration guide on said straight portions, and a groove along a portion of an outer surface to indicate an angular direction of 0, wherein said groove does not extend over the outer surface of said fixtures.

17. The method of claim 16, wherein extracting from said calibration object further comprises:
finding a last frame in which an interference intensity from said first fixture appears, and a first frame in which an interference intensity from said groove appears;
selecting a center line of said groove from said first frame in which said groove appears as defining a starting angular direction of 0;
determining the frame number of said first frame in which said groove appears from a length of one of said straight portions of said scanning guide and a speed of said probe, said frame number defining a starting position;
for each scan line, finding a pixel number of a maximum interference intensity value, and determining an offset distance of said pixel from said scan guide; and
reconstructing said a surface of said calibration object from said distance offset data.

18. A program storage device readable by a computer, tangibly embodying a program of instructions executable by the computer to perform the method steps for reconstructing an ear canal, comprising the steps of:
providing a set of optical coherence tomography (OCT) scan data of an ear comprising frames and scan lines of pixels that form a 3D data set whose values are interference intensities;
extracting frame numbers and line numbers of interference intensities corresponding to one or more markers on an OCT scan guide;
receiving reference frame numbers and lines numbers for said one or more markers;
determining a starting position and direction for said OCT ear scan from the ear scan marker frame and line numbers and said reference marker frame and line numbers;
for each scan line, finding a pixel number of a maximum interference intensity value, and determining an offset distance of said pixel from said scan guide; and
reconstructing said surface of said ear canal from said distance offset data.

19. The computer readable program storage device of claim 18, wherein an offset distance d of a pixel j from the guide is computed from $$d(j) = d_0 + \frac{j}{d_s},$$

wherein $d_0$ is an offset from the center of the guide and $d_s$ is a sampling rate.

20. The computer readable program storage device of claim 18, wherein said ear canal surface can be reconstructed from $$\vec{p}(i,j) = \vec{p}_0 + \vec{c}(t) + d(j)(\sin(\alpha)\vec{u} + \cos(\alpha)\vec{v}),$$

wherein $\vec{p}(i,j)$ represents a scan line i perpendicular to guide, j a pixel along the scan line, $\vec{p}_0$ is a starting position in space of the scan, $\vec{c}(t)$ a curved path of the wide, t is a position on the guide corresponding to the scan line i, and $\alpha$ is a scan line angle, and $\vec{u}$ and $\vec{v}$ are two unit vectors perpendicular to each other defining a 2D coordinate frame in a plane perpendicular to the curve $\vec{c}(t)$.

21. The computer readable program storage device of claim 20, wherein $$t = i \cdot \frac{v}{f},$$

wherein v is a scan speed of a scanning probe contained within said guide, and f is a scan line sampling frequency, and $$\alpha = i \cdot \frac{\omega}{f},$$

wherein $\omega$ is the angular speed of rotation the probe.

22. The computer readable program storage device of claim 20, wherein said unit vectors $\vec{u}$ and $\vec{v}$ are defined by $$\vec{u} = \frac{\vec{t} \times \vec{w}}{|\vec{t} \times \vec{w}|},$$

$$\vec{v} = \vec{t} \times \vec{u},$$

wherein $\vec{w}$ is a vector that is not perpendicular to the curve $\vec{c}(t)$ at any time, and $\vec{t}$ is a tangent to the curve defined as $$\vec{t} = \frac{d}{dt}\vec{c}(t).$$

23. The computer readable program storage device of claim 18, wherein said OCT scan data is obtained by providing an OCT scanning apparatus including a guide containing a rotatable probe, sliding and rotating said probe in said guide, emitting near infrared light from said probe at predetermined intervals, measuring interference of reflected light with a reference signal, and saving said interference data in a computer readable storage medium.

24. The computer readable program storage device of claim 18, said method comprising, for each scan line, selecting those pixels with an interference intensity value above a pre-determined threshold and determining an offset distance of said selected pixels from said scan guide.

25. The computer readable program storage device of claim 18, said method comprising, prior to finding a pixel number of a maximum interference intensity value for a scan line, discarding the intensity values at the beginning of a scan line, wherein said beginning values correspond to reflections from the scan guide itself.

26. The computer readable program storage device of claim 18, wherein said reference marker frame numbers and lines numbers were extracted from OCT scan data of a calibration object.

27. The computer readable program storage device of claim 26, wherein extracting said reference marker frame numbers and lines numbers from OCT scan data of a calibration object comprises:
providing a set of optical coherence tomography (OCT) scan data of a calibration object marked to indicate an angular direction of 0, said scan data comprising frames and scan lines of pixels that form a 3D data set whose values are interference intensities acquired using a calibration guide comprising one or more markers on said guide;
extracting frame numbers and line numbers of interference intensities corresponding to said markers on said calibration guide; and
determining spatial positions of said markers on said calibration guide from said frame number and said line numbers.

28. The computer readable program storage device of claim 27, wherein said marker positions on the guide are calculated from:

$$\alpha_{marker} = \begin{cases} 2\pi - (n_{S_{\alpha=0}} - n_{S_{marker}}) \cdot d_\alpha, & \text{if } n_{S_{\alpha=0}} > n_{S_{marker}} \\ (n_{S_{marker}} - n_{S_{\alpha=0}}) \cdot d_\alpha, & \text{if } n_{S_{\alpha=0}} \leq n_{S_{marker}} \end{cases}$$

$$t_{marker} = ((n_{F_{marker}} - n_{F_{start}}) \cdot N + n_{S_{marker}} - n_{S_{start}})) \cdot \Delta t,$$

wherein $\alpha$ is an angle of rotation about said guide, $\alpha_{marker}$ is an angular direction of a marker, $t_{marker}$ is the frame number of the marker, $n_{S_{\alpha=0}}$ is a line number of a scan line at an angular direction of 0, $n_{S_{start}}$ is a starting line number, $n_{S_{marker}}$ is a line number of a scan line that contains marker interference intensity values, $n_{F_{start}}$ is a starting frame number, $n_{F_{marker}}$ is a frame number of a frame containing marker interference intensity values, $d_\alpha$ is an angular increment, N is a number of lines per frame, and $\Delta t$ is a resolution along the scan path.

29. The computer readable program storage device of claim 18, wherein the starting position $t_{start}$ and direction $\alpha_{start}$ are computed from a marker position $t_{marker}$ and direction $\alpha_{marker}$ from $$\alpha_{start} = \begin{cases} \alpha_{marker} - n_{S_{marker}} \cdot d_\alpha, & \text{if } \alpha_{marker} - n_{S_{marker}} \cdot d_\alpha \geq 0, \\ 2\pi + \alpha_{marker} - n_{S_{marker}} \cdot d_\alpha, & \text{if } \alpha_{marker} - n_{S_{marker}} \cdot d_\alpha < 0, \end{cases}$$

$$t_{start} = t_{marker} - ((n_{F_{marker}} - 1) \cdot N + n_{S_{marker}}) \cdot \Delta t,$$

wherein $n_{S_{marker}}$ is a line number of a scan line that contains marker interference intensity values, $n_{F_{marker}}$ is a frame number of a frame containing marker interference intensity values, $d_\alpha$ is an angular increment, N is a number of lines per frame, and $\Delta t$ is a resolution along the scan path.

* * * * *